United States Patent
Stoynova et al.

(10) Patent No.: US 9,175,319 B2
(45) Date of Patent: Nov. 3, 2015

(54) METHOD FOR PRODUCING AN L-AMINO ACID USING A BACTERIUM OF THE FAMILY ENTEROBACTERIACEAE HAVING ATTENUATED EXPRESSION OF THE YJJK GENE

(71) Applicant: AJINOMOTO CO., INC., Tokyo (JP)

(72) Inventors: Natalia Viktorovna Stoynova, Moscow (RU); Valery Vasilievich Samsonov, Podolsk (RU); Natalia Sergeevna Eremina, Moscow (RU); Evgeniya Aleksandrovna Polyakova, Moscow (RU)

(73) Assignee: AJINOMOTO CO., INC., Tokyo (JP)

(*) Notice: Subject to any disclaimer, the term of this patent is extended or adjusted under 35 U.S.C. 154(b) by 0 days.

(21) Appl. No.: 14/259,365

(22) Filed: Apr. 23, 2014

(65) Prior Publication Data

US 2014/0315261 A1 Oct. 23, 2014

(30) Foreign Application Priority Data

Apr. 23, 2013 (RU) ................ 2013118637

(51) Int. Cl.

| | |
|---|---|
| *C12P 13/04* | (2006.01) |
| *C12P 13/22* | (2006.01) |
| *C12P 13/06* | (2006.01) |
| *C12P 13/08* | (2006.01) |
| *C12P 13/10* | (2006.01) |
| *C12P 13/12* | (2006.01) |
| *C12P 13/14* | (2006.01) |
| *C12P 13/20* | (2006.01) |
| *C12P 13/24* | (2006.01) |

(52) U.S. Cl.
CPC ........... *C12P 13/04* (2013.01); *C12P 13/06* (2013.01); *C12P 13/08* (2013.01); *C12P 13/10* (2013.01); *C12P 13/12* (2013.01); *C12P 13/14* (2013.01); *C12P 13/20* (2013.01); *C12P 13/22* (2013.01); *C12P 13/222* (2013.01); *C12P 13/225* (2013.01); *C12P 13/227* (2013.01); *C12P 13/24* (2013.01)

(58) Field of Classification Search
None
See application file for complete search history.

(56) References Cited

U.S. PATENT DOCUMENTS

| | | | |
|---|---|---|---|
| 4,278,765 A | 7/1981 | Debabov et al. | |
| 4,346,170 A | 8/1982 | Sano et al. | |
| 5,661,012 A | 8/1997 | Sano et al. | |
| 5,965,391 A | 10/1999 | Reinscheid et al. | |
| 5,998,178 A | 12/1999 | Hashiguchi et al. | |
| 6,040,160 A | 3/2000 | Kojima et al. | |
| 8,460,903 B2 | 6/2013 | Savrasova et al. | |
| 2006/0216796 A1 | 9/2006 | Hashiguchi et al. | |
| 2009/0162908 A1 | 6/2009 | Yampolskaya et al. | |
| 2009/0197309 A1 | 8/2009 | Sycheva et al. | |
| 2012/0237986 A1 | 9/2012 | Ziyatdinov et al. | |
| 2013/0224806 A1 | 8/2013 | Savrasova et al. | |

OTHER PUBLICATIONS

Panina et al., "Proceedings of the Third International Conference on Bioinformatics of Genome Regulation and Structure", vol. 2, pp. 29-31, 2002.*
Brenner, S., Trends in Genomics 15:132-133, 1999.*
Murat et al., J. Biol. Chem. 281:6850-6859, 2006.*
Cohen et al., J. Bacteriol. 67:182-190, 1954.*
Link, A. J., et al., "Comparing the predicted and observed properties of proteins encoded in the genome of *Escherichia coli* K-12," Electrophoresis 1997;18:1259-1313.
Linton, K. J., et al., "The *Escherichia coli* ATP-binding cassette (ABC) proteins," Mol. Microbiol. 1998;28(1):5-13.
Rees, D. C., et al., "ABC transporters: The power to change," Nat. Rev. Mol. Cell Biol. 2009;10(3):218-227.
Boël, G., et al., "The ABC-F protein EttA gates ribosome entry into the translation elongation cycle," Nature Structural & Molecular Biology 2014;21(2):143-151.
Chen, B., et al., "EttA regulates translation by binding the ribosomal E site and restricting ribosome-tRNA dynamics," Nature Structural & Molecular Biology 2014;21(2):152-159.
Frederick, K., et al., "The ABCs of the ribosome," Nature Structural & Molecular Biology 2014;21(2):115-116.
Murat, D., et al., "Deletion of the *Escherichia coli* uup gene encoding a protein of the ATP binding cassette superfamily affects bacterial competitiveness," Research in Microbiology 2008;159:671-677.
"Protein function discovery could advance antibiotic development," University of Lethbridge, Alberta, Canada, Feb. 24, 2014, pp. 1-2; http://www.uleth.ca/unews/article/protein-function-discovery-could-advance-antibiotic-development; retrieved from www on Aug. 15, 2014.
Extended European Search Report for European Patent App. No. 14165592.8 (Sep. 1, 2014).

* cited by examiner

*Primary Examiner* — David J Steadman
(74) *Attorney, Agent, or Firm* — Shelly Guest Cermak; Cermak Nakajima & McGowan LLP

(57) ABSTRACT

The present invention provides a method for producing L-amino acids by fermentation using a bacterium of the family Enterobacteriaceae, particularly a bacterium belonging to the genus *Escherichia*, which has been modified to attenuate expression of the yjjK gene.

6 Claims, No Drawings

SEQUENCE LISTING

<160> NUMBER OF SEQ ID NOS: 9

<210> SEQ ID NO 1
<211> LENGTH: 1668
<212> TYPE: DNA
<213> ORGANISM: Escherichia coli

<400> SEQUENCE: 1

```
gtg gct caa ttc gtt tat acc atg cat cgt gtc ggc aaa gtt gtt ccg        48
Val Ala Gln Phe Val Tyr Thr Met His Arg Val Gly Lys Val Val Pro
1               5                   10                  15 ccg aaa cgt cat att ttg aaa aac atc tct ctg agt ttc ttc cct ggg        96
Pro Lys Arg His Ile Leu Lys Asn Ile Ser Leu Ser Phe Phe Pro Gly
            20                  25                  30 gca aaa att ggt gtc ctg ggt ctg aat ggc gcg ggt aag tcc acc ctg       144
Ala Lys Ile Gly Val Leu Gly Leu Asn Gly Ala Gly Lys Ser Thr Leu
        35                  40                  45 ctg cgc att atg gcg ggc att gat aaa gac atc gaa ggt gaa gcg cgt       192
Leu Arg Ile Met Ala Gly Ile Asp Lys Asp Ile Glu Gly Glu Ala Arg
    50                  55                  60 ccg cag cca gac atc aag att ggt tat ctg ccg cag gaa ccg cag ctg       240
Pro Gln Pro Asp Ile Lys Ile Gly Tyr Leu Pro Gln Glu Pro Gln Leu
```

-continued

```
           65                  70                  75                  80
aac ccg gaa cac acc gtg cgt gag tcc att gaa gaa gcg gtt tca gaa      288
Asn Pro Glu His Thr Val Arg Glu Ser Ile Glu Glu Ala Val Ser Glu
                85                  90                  95 gtg gtt aac gcc ctg aaa cgc ctg gat gaa gtg tat gcg ctg tac gcc      336
Val Val Asn Ala Leu Lys Arg Leu Asp Glu Val Tyr Ala Leu Tyr Ala
            100                 105                 110 gat ccg gat gcc gat ttt gac aag ctg gcc gct gaa caa ggc cgt ctg      384
Asp Pro Asp Ala Asp Phe Asp Lys Leu Ala Ala Glu Gln Gly Arg Leu
            115                 120                 125 gaa gag atc att cag gct cac gac ggt cat aat ctg aac gta cag ctg      432
Glu Glu Ile Ile Gln Ala His Asp Gly His Asn Leu Asn Val Gln Leu
        130                 135                 140 gag cgt gcg gcg gat gcg cta cgt ctg ccg gac tgg gac gcg aaa atc      480
Glu Arg Ala Ala Asp Ala Leu Arg Leu Pro Asp Trp Asp Ala Lys Ile
145                 150                 155                 160 gct aac ctc tcc ggt ggt gaa cgt cgt gcg gta gcg ttg tgc cgc ctg      528
Ala Asn Leu Ser Gly Gly Glu Arg Arg Val Ala Leu Cys Arg Leu
                165                 170                 175 ctg ctg gaa aaa cca gac atg ctg ctc ctc gac gaa ccg acc aac cac      576
Leu Leu Glu Lys Pro Asp Met Leu Leu Leu Asp Glu Pro Thr Asn His
            180                 185                 190 ctg gat gcc gaa tcc gtg gcc tgg ctg gaa cgc ttc ctg cac gac ttc      624
Leu Asp Ala Glu Ser Val Ala Trp Leu Glu Arg Phe Leu His Asp Phe
            195                 200                 205 gaa ggc acc gtt gtg gcg att acc cac gac cgt tac ttc ctc gat aac      672
Glu Gly Thr Val Val Ala Ile Thr His Asp Arg Tyr Phe Leu Asp Asn
        210                 215                 220 gtt gca ggc tgg atc ctc gaa ctt gac cgc ggt gaa ggt att ccg tgg      720
Val Ala Gly Trp Ile Leu Glu Leu Asp Arg Gly Glu Gly Ile Pro Trp
225                 230                 235                 240 gaa ggt aac tac tcc tcc tgg ctg gag cag aaa gat cag cgc ctg gcg      768
Glu Gly Asn Tyr Ser Ser Trp Leu Glu Gln Lys Asp Gln Arg Leu Ala
                245                 250                 255 cag gaa gct tca caa gaa gcg gcg cgt cgt aag tcg att gag aaa gag      816
Gln Glu Ala Ser Gln Glu Ala Ala Arg Arg Lys Ser Ile Glu Lys Glu
            260                 265                 270 ctg gaa tgg gta cgt caa ggt act aaa ggc cgt cag tcg aaa ggt aaa      864
Leu Glu Trp Val Arg Gln Gly Thr Lys Gly Arg Gln Ser Lys Gly Lys
            275                 280                 285 gca cgt ctg gcg cgc ttt gaa gaa ctg aac agc acc gaa tat cag aaa      912
Ala Arg Leu Ala Arg Phe Glu Glu Leu Asn Ser Thr Glu Tyr Gln Lys
        290                 295                 300 cgt aac gaa acc aac gaa ctg ttt att cca cct gga ccg cgt ctg ggc      960
Arg Asn Glu Thr Asn Glu Leu Phe Ile Pro Pro Gly Pro Arg Leu Gly
305                 310                 315                 320 gat aaa gtg ctg gaa gtc agc aac ctg cgt aaa tcc tat ggc gat cgt     1008
Asp Lys Val Leu Glu Val Ser Asn Leu Arg Lys Ser Tyr Gly Asp Arg
                325                 330                 335 ctg ctg att gat gac ctg agc ttc tcg atc ccg aaa gga gcg atc gtc     1056
Leu Leu Ile Asp Asp Leu Ser Phe Ser Ile Pro Lys Gly Ala Ile Val
            340                 345                 350 ggg atc atc ggt ccg aac ggt gcg ggt aaa tcg acc ctg ttc cgt atg     1104
Gly Ile Ile Gly Pro Asn Gly Ala Gly Lys Ser Thr Leu Phe Arg Met
            355                 360                 365 atc tct ggt cag gaa cag ccg gac agc ggc acc atc act ttg ggt gaa     1152
Ile Ser Gly Gln Glu Gln Pro Asp Ser Gly Thr Ile Thr Leu Gly Glu
        370                 375                 380 acg gtg aaa ctg gcg tcg gtt gat cag ttc cgt gac tca atg gat aac     1200
```

```
                Thr Val Lys Leu Ala Ser Val Asp Gln Phe Arg Asp Ser Met Asp Asn
                385                 390                 395                 400 agc aaa acc gtt tgg gaa gaa gtt tcc ggc ggg ctg gat atc atg aag         1248
Ser Lys Thr Val Trp Glu Glu Val Ser Gly Gly Leu Asp Ile Met Lys
                    405                 410                 415 atc ggc aac acc gag atg cca agc cgc gcc tac gtt ggc cgc ttt aac         1296
Ile Gly Asn Thr Glu Met Pro Ser Arg Ala Tyr Val Gly Arg Phe Asn
                420                 425                 430 ttt aaa ggg gtt gat cag ggt aaa cgc gtt ggt gaa ctc tcc ggt ggt         1344
Phe Lys Gly Val Asp Gln Gly Lys Arg Val Gly Glu Leu Ser Gly Gly
            435                 440                 445 gag cgc ggt cgt ctg cat ctg gcg aag ctg ctg cag gtt ggc ggc aac         1392
Glu Arg Gly Arg Leu His Leu Ala Lys Leu Leu Gln Val Gly Gly Asn
        450                 455                 460 atg ctg ctg ctc gac gaa cca acc aac gac ctg gat atc gaa acc ctg         1440
Met Leu Leu Leu Asp Glu Pro Thr Asn Asp Leu Asp Ile Glu Thr Leu
465                 470                 475                 480 cgc gcg ctg gaa aac gcc ctg ctg gag ttc ccg ggc tgt gcg atg gtt         1488
Arg Ala Leu Glu Asn Ala Leu Leu Glu Phe Pro Gly Cys Ala Met Val
                485                 490                 495 atc tcg cac gac cgt tgg ttc ctc gac cgt atc gcc acg cac att ctg         1536
Ile Ser His Asp Arg Trp Phe Leu Asp Arg Ile Ala Thr His Ile Leu
            500                 505                 510 gat tac cag gat gaa ggt aaa gtt gag ttc ttc gaa ggt aac ttt acc         1584
Asp Tyr Gln Asp Glu Gly Lys Val Glu Phe Phe Glu Gly Asn Phe Thr
        515                 520                 525 gag tac gaa gag tac aag aaa cgc acg ctg ggc gca gac gcg ctg gag         1632
Glu Tyr Glu Glu Tyr Lys Lys Arg Thr Leu Gly Ala Asp Ala Leu Glu
530                 535                 540 ccg aag cgt atc aag tac aag cgt att gcg aag taa                         1668
Pro Lys Arg Ile Lys Tyr Lys Arg Ile Ala Lys
545                 550                 555

<210> SEQ ID NO 2
<211> LENGTH: 555
<212> TYPE: PRT
<213> ORGANISM: Escherichia coli

<400> SEQUENCE: 2

Met Ala Gln Phe Val Tyr Thr Met His Arg Val Gly Lys Val Pro
1               5                   10                  15

Pro Lys Arg His Ile Leu Lys Asn Ile Ser Leu Ser Phe Phe Pro Gly
                20                  25                  30

Ala Lys Ile Gly Val Leu Gly Leu Asn Gly Ala Gly Lys Ser Thr Leu
            35                  40                  45

Leu Arg Ile Met Ala Gly Ile Asp Lys Asp Ile Glu Gly Glu Ala Arg
        50                  55                  60

Pro Gln Pro Asp Ile Lys Ile Gly Tyr Leu Pro Gln Glu Pro Gln Leu
65                  70                  75                  80

Asn Pro Glu His Thr Val Arg Glu Ser Ile Glu Glu Ala Val Ser Glu
                85                  90                  95

Val Val Asn Ala Leu Lys Arg Leu Asp Glu Val Tyr Ala Leu Tyr Ala
                100                 105                 110

Asp Pro Asp Ala Asp Phe Asp Lys Leu Ala Ala Glu Gln Gly Arg Leu
            115                 120                 125

Glu Glu Ile Ile Gln Ala His Asp Gly His Asn Leu Asn Val Gln Leu
        130                 135                 140

Glu Arg Ala Ala Asp Ala Leu Arg Leu Pro Asp Trp Asp Ala Lys Ile
```

```
            145                 150                 155                 160
        Ala Asn Leu Ser Gly Gly Glu Arg Arg Val Ala Leu Cys Arg Leu
                        165                 170                 175

Leu Leu Glu Lys Pro Asp Met Leu Leu Leu Asp Glu Pro Thr Asn His
                        180                 185                 190

Leu Asp Ala Glu Ser Val Ala Trp Leu Glu Arg Phe Leu His Asp Phe
                        195                 200                 205

Glu Gly Thr Val Val Ala Ile Thr His Asp Arg Tyr Phe Leu Asp Asn
                        210                 215                 220

Val Ala Gly Trp Ile Leu Glu Leu Asp Arg Gly Glu Gly Ile Pro Trp
        225                 230                 235                 240

Glu Gly Asn Tyr Ser Ser Trp Leu Glu Gln Lys Asp Gln Arg Leu Ala
                        245                 250                 255

Gln Glu Ala Ser Gln Glu Ala Ala Arg Arg Lys Ser Ile Glu Lys Glu
                        260                 265                 270

Leu Glu Trp Val Arg Gln Gly Thr Lys Gly Arg Gln Ser Lys Gly Lys
                        275                 280                 285

Ala Arg Leu Ala Arg Phe Glu Glu Leu Asn Ser Thr Glu Tyr Gln Lys
        290                 295                 300

Arg Asn Glu Thr Asn Glu Leu Phe Ile Pro Pro Gly Pro Arg Leu Gly
        305                 310                 315                 320

Asp Lys Val Leu Glu Val Ser Asn Leu Arg Lys Ser Tyr Gly Asp Arg
                        325                 330                 335

Leu Leu Ile Asp Asp Leu Ser Phe Ser Ile Pro Lys Gly Ala Ile Val
                        340                 345                 350

Gly Ile Ile Gly Pro Asn Gly Ala Gly Lys Ser Thr Leu Phe Arg Met
                        355                 360                 365

Ile Ser Gly Gln Glu Gln Pro Asp Ser Gly Thr Ile Thr Leu Gly Glu
                        370                 375                 380

Thr Val Lys Leu Ala Ser Val Asp Gln Phe Arg Asp Ser Met Asp Asn
        385                 390                 395                 400

Ser Lys Thr Val Trp Glu Glu Val Ser Gly Gly Leu Asp Ile Met Lys
                        405                 410                 415

Ile Gly Asn Thr Glu Met Pro Ser Arg Ala Tyr Val Gly Arg Phe Asn
                        420                 425                 430

Phe Lys Gly Val Asp Gln Gly Lys Arg Val Gly Glu Leu Ser Gly Gly
                        435                 440                 445

Glu Arg Gly Arg Leu His Leu Ala Lys Leu Leu Gln Val Gly Gly Asn
                        450                 455                 460

Met Leu Leu Leu Asp Glu Pro Thr Asn Asp Leu Asp Ile Glu Thr Leu
        465                 470                 475                 480

Arg Ala Leu Glu Asn Ala Leu Leu Glu Phe Pro Gly Cys Ala Met Val
                        485                 490                 495

Ile Ser His Asp Arg Trp Phe Leu Asp Arg Ile Ala Thr His Ile Leu
                        500                 505                 510

Asp Tyr Gln Asp Glu Gly Lys Val Glu Phe Phe Glu Gly Asn Phe Thr
                        515                 520                 525

Glu Tyr Glu Glu Tyr Lys Lys Arg Thr Leu Gly Ala Asp Ala Leu Glu
                        530                 535                 540

Pro Lys Arg Ile Lys Tyr Lys Arg Ile Ala Lys
        545                 550                 555

<210> SEQ ID NO 3
```

```
<211> LENGTH: 60
<212> TYPE: DNA
<213> ORGANISM: Artificial Sequence
<220> FEATURE:
<223> OTHER INFORMATION: Primer P1

<400> SEQUENCE: 3
attatcacga taaacataga ggcgaagtcc aacgtggaaa ggtcattttt cctgaatatg     60

<210> SEQ ID NO 4
<211> LENGTH: 61
<212> TYPE: DNA
<213> ORGANISM: Artificial Sequence
<220> FEATURE:
<223> OTHER INFORMATION: Primer P2

<400> SEQUENCE: 4
ccggcatttt acgcattact tcgcaatacg cttgtatcgt tgttgacag ctggtccaat     60
g                                                                    61

<210> SEQ ID NO 5
<211> LENGTH: 1922
<212> TYPE: DNA
<213> ORGANISM: Artificial Sequence
<220> FEATURE:
<223> OTHER INFORMATION: PCR product 1

<400> SEQUENCE: 5
attatcacga taaacataga ggcgaagtcc aacgtggaaa ggtcattttt cctgaatatg     60
ctcacatcat ataagaaat acagataaag ttattatctg cttgtggtgg tgaatgcact    120
gaccggctat aaggaaaggc caaacaagac acggttgcaa aaaccgtgcc cttaaatatt    180
gaatctctat tcagaacact tcttaaatt gtcatttggc atattacgaa caattccgcg    240
taaaaacgtt ctgttacgct aaaccccttat ccagcaggct ttcaaggatg taaaccataa    300
cactctgcga actagtgtta cattgcgtgt agctttgagt gggcaacttt gtgtacactt    360
ttgtgtaccc aaaaacaaaa atgtgtaccc attcaatgat ggatccgcgg ccgcgggggg    420 ggggaaagc cacgttgtgt ctcaaaatct ctgatgttac attgcacaag ataaaaatat    480
atcatcatga acaataaaac tgtctgctta cataaacagt aatacaaggg gtgttatgag    540
ccatattcaa cgggaaacgt cttgctcgag gccgcgatta aattccaaca tggatgctga    600
tttatatggg tataaatggg ctcgcgataa tgtcgggcaa tcaggtgcga caatctatcg    660
attgtatggg aagcccgatg cgccagagtt gtttctgaaa catggcaaag gtagcgttgc    720
caatgatgtt acagatgaga tggtcagact aaactggctg acggaattta tgcctcttcc    780
gaccatcaag catttttatcc gtactcctga tgatgcatgg ttactcacca ctgcgatccc    840
cgggaaaaca gcattccagg tattagaaga atatcctgat tcaggtgaaa atattgttga    900
tgcgctggca gtgttcctgc gccggttgca ttcgattcct gtttgtaatt gtccttttaa    960
cagcgatcgc gtatttcgtc tcgctcaggc gcaatcacga atgaataacg gtttggttga   1020
tgcgagtgat tttgatgacg agcgtaatgg ctggcctgtt gaacaagtct ggaaagaaat   1080
gcataagctt ttgccattct caccggattc agtcgtcact catggtgatt tctcacttga   1140
taaccttatt tttgacgagg ggaaattaat aggttgtatt gatgttggac gagtcggaat   1200
cgcagaccga taccaggatc ttgccatcct atggaactgc ctcggtgagt tttctccttc   1260
attacagaaa cggctttttc aaaaatatgg tattgataat cctgatatga ataaattgca   1320
gtttcatttg atgctcgatg agttttctca aattaccctg ttatccctat ctagagattt   1380
```

```
gaatagcgag cgtaccttag cagggctggc cgtagccagg caaaagggcg agttggtggt   1440
cgcaggccta agttcacgga tgagcaatgg cgggaaatgg gggagcggat ggcaaccggt   1500
gaatcacgac aaagcgtatc aaaaacgtat ggagtagggc tctaaactct gtataaaaag   1560
tttccagcta gctgataacg ggaaagaaac agagaagggc acaaatattg tgtactttaa   1620
tgtgcccttt aatttattga ttggtggttg aattgtccgt aacttttttga tttaagtgca   1680 aatttctaat aaattagaac actttcttaa atggtttcac tgaaacgtgt tcatagactc   1740
ctgccgctac gtacgggtca gcatcggccc aggcctgagc tgcttccagc gattcaaatt   1800
cagcaataac ggttgagcca gtaaatcccg cagcccctgg atcgttactg tctaccgctg   1860
gcattggacc agctgtcaac aaacgataca agcgtattgc gaagtaatgc gtaaaatgcc   1920
gg                                                                 1922

<210> SEQ ID NO 6
<211> LENGTH: 21
<212> TYPE: DNA
<213> ORGANISM: Artificial Sequence
<220> FEATURE:
<223> OTHER INFORMATION: Primer P3

<400> SEQUENCE: 6
tacacttcgc ctttgaaaac t                                            21

<210> SEQ ID NO 7
<211> LENGTH: 21
<212> TYPE: DNA
<213> ORGANISM: Artificial Sequence
<220> FEATURE:
<223> OTHER INFORMATION: Primer P4

<400> SEQUENCE: 7
tgaaattgct ggttttgtag g                                            21

<210> SEQ ID NO 8
<211> LENGTH: 1783
<212> TYPE: DNA
<213> ORGANISM: Artificial Sequence
<220> FEATURE:
<223> OTHER INFORMATION: PCR product 2

<400> SEQUENCE: 8
tacacttcgc ctttgaaaac tcattatcac gataaacata gaggcgaagt ccaacgtggc   60
tcaattcgtt tataccatgc atcgtgtcgg caaagttgtt ccgccgaaac gtcatatttt   120
gaaaaacatc tctctgagtt tcttccctgg ggcaaaaatt ggtgtcctgg gtctgaatgg   180
cgcgggtaag tccaccctgc tgcgcattat ggcgggcatt gataaagaca tcgaaggtga   240
agcgcgtccg cagccagaca tcaagattgg ttatctgccg caggaaccgc agctgaaccc   300
ggaacacacc gtgcgtgagt ccattgaaga agcggtttca gaagtggtta acgccctgaa   360
acgcctggat gaagtgtatg cgctgtacgc cgatccggat gccgatttttg acaagctggc   420 cgctgaacaa ggccgtctgg aagagatcat tcaggctcac gacggtcata atctgaacgt   480
acagctggag cgtgcggcgg atgcgctacg tctgccggac tgggacgcga aaatcgctaa   540
cctctccggt ggtgaacgtc gtcgcgtagc gttgtgccgc ctgctgctgg aaaaaccaga   600
catgctgctg ctcgacgaac cgaccaacca cctggatgcc gaatccgtgg cctggctgga   660
acgcttcctg cacgacttcg aaggcaccgt tgtggcgatt acccacgacc gttacttcct   720
```

-continued

| | |
|---|---|
| cgataacgtt gcaggctgga tcctcgaact tgaccgcggt gaaggtattc cgtgggaagg | 780 |
| taactactcc tcctggctgg agcagaaaga tcagcgcctg gcgcaggaag cttcacaaga | 840 |
| agcggcgcgt cgtaagtcga ttgagaaaga gctggaatgg gtacgtcaag gtactaaagg | 900 |
| ccgtcagtcg aaaggtaaag cacgtctggc gcgctttgaa gaactgaaca gcaccgaata | 960 |
| tcagaaacgt aacgaaacca cgaactgtt tattccacct ggaccgcgtc tgggcgataa | 1020 |
| agtgctggaa gtcagcaacc tgcgtaaatc ctatggcgat cgtctgctga ttgatgacct | 1080 |
| gagcttctcg atcccgaaag gagcgatcgt cgggatcatc ggtccgaacg gtgcgggtaa | 1140 |
| atcgaccctg ttccgtatga tctctggtca ggaacagccg gacagcggca ccatcacttt | 1200 |
| gggtgaaacg gtgaaactgg cgtcggttga tcagttccgt gactcaatgg ataacagcaa | 1260 |
| aaccgtttgg gaagaagttt ccggcgggct ggatatcatg aagatcggca acaccgagat | 1320 |
| gccaagccgc gcctacgttg gccgctttaa ctttaaaggg gttgatcagg gtaaacgcgt | 1380 |
| tggtgaactc tccggtggtg agcgcggtcg tctgcatctg gcgaagctgc tgcaggttgg | 1440 |
| cggcaacatg ctgctgctcg acgaaccaac caacgacctg gatatcgaaa ccctgcgcgc | 1500 |
| gctggaaaac gccctgctgg agttcccggg ctgtgcgatg gttatctcgc acgaccgttg | 1560 |
| gttcctcgac cgtatcgcca cgcacattct ggattaccag gatgaaggta agttgagtt | 1620 |
| cttcgaaggt aactttaccg agtacgaaga gtacaagaaa cgcacgctgg gcgcagacgc | 1680 |
| gctggagccg aagcgtatca agtacaagcg tattgcgaag taatgcgtaa aatgccggat | 1740 |
| gcggcgcgaa cgccttatcc ggcctacaaa accagcaatt tca | 1783 |

<210> SEQ ID NO 9
<211> LENGTH: 1989
<212> TYPE: DNA
<213> ORGANISM: Artificial Sequence
<220> FEATURE:
<223> OTHER INFORMATION: PCR product 3

<400> SEQUENCE: 9

| | |
|---|---|
| tacacttcgc ctttgaaaac tcattatcac gataaacata gaggcgaagt ccaacgtgga | 60 |
| aaggtcattt ttcctgaata tgctcacatc atataaagaa atacagataa agttattatc | 120 |
| tgcttgtggt ggtgaatgca ctgaccggct ataaggaaag gccaaacaag acacggttgc | 180 |
| aaaaaccgtg cccttaaata ttgaatctct attcagaaca cttttcttaaa ttgtcatttg | 240 |
| gcatattacg aacaattccg cgtaaaaacg ttctgttacg ctaaacccctt atccagcagg | 300 |
| ctttcaagga tgtaaaccat aacactctgc gaactagtgt tacattgcgt gtagctttga | 360 |
| gtgggcaact ttgtgtacac ttttgtgtac ccaaaaacaa aaatgtgtac ccattcaatg | 420 |
| atggatccgc ggccgcgggg ggggggaaaa gccacgttgt gtctcaaaat ctctgatgtt | 480 |
| acattgcaca agataaaaat atatcatcat gaacaataaa actgtctgct tacataaaca | 540 |
| gtaatacaag gggtgttatg agccatattc aacgggaaac gtcttgctcg aggccgcgat | 600 |
| taaattccaa catggatgct gatttatatg ggtataaatg ggctcgcgat aatgtcgggc | 660 |
| aatcaggtgc gacaatctat cgattgtatg ggaagcccga tgcgccagag ttgtttctga | 720 |
| aacatggcaa aggtagcgtt gccaatgatg ttacagatga gatggtcaga ctaaactggc | 780 |
| tgacggaatt tatgcctctt ccgaccatca agcattttat ccgtactcct gatgatgcat | 840 |
| ggttactcac cactgcgatc cccgggaaaa cagcattcca ggtattagaa gaatatcctg | 900 |
| attcaggtga aaatattgtt gatgcgctgg cagtgttcct gcgccggttg cattcgattc | 960 |
| ctgtttgtaa ttgtccttt aacagcgatc gcgtatttcg tctcgctcag gcgcaatcac | 1020 |

```
gaatgaataa cggtttggtt gatgcgagtg attttgatga cgagcgtaat ggctggcctg    1080
ttgaacaagt ctggaaagaa atgcataagc ttttgccatt ctcaccggat tcagtcgtca    1140
ctcatggtga tttctcactt gataacctta tttttgacga ggggaaatta ataggttgta    1200
ttgatgttgg acgagtcgga atcgcagacc gataccagga tcttgccatc ctatggaact    1260
gcctcggtga gttttctcct tcattacaga aacggctttt tcaaaaatat ggtattgata    1320
atcctgatat gaataaattg cagtttcatt tgatgctcga tgagtttttc taaattaccc    1380
tgttatccct atctagagat ttgaatagcg agcgtacctt agcagggctg gccgtagcca    1440
ggcaaaaggg cgagttggtg gtcgcaggcc taagttcacg gatgagcaat ggcgggaaat    1500
gggggagcgg atggcaaccg gtgaatcacg acaaagcgta tcaaaaacgt atggagtagg    1560
gctctaaact ctgtataaaa agtttccagc tagctgataa cggaaaagaa acagagaagg    1620
gcacaaatat tgtgtacttt aatgtgccct ttaatttatt gattggtggt tgaattgtcc    1680 gtaactttt gatttaagtg caaatttcta ataaattaga acactttctt aaatggtttc    1740
actgaaacgt gttcatagac tcctgccgct acgtacgggt cagcatcggc ccaggcctga    1800
gctgcttcca gcgattcaaa ttcagcaata acggttgagc cagtaaatcc cgcagcccct    1860
ggatcgttac tgtctaccgc tggcattgga ccagctgtca acaaacgata caagcgtatt    1920
gcgaagtaat gcgtaaaatg ccggatgcgg cgcgaacgcc ttatccggcc tacaaaacca    1980
gcaatttca                                                            1989
```

METHOD FOR PRODUCING AN L-AMINO ACID USING A BACTERIUM OF THE FAMILY ENTEROBACTERIACEAE HAVING ATTENUATED EXPRESSION OF THE YJJK GENE

This application claims priority under 35 U.S.C. §119 to Russian Patent Application No. 2013118637, filed Apr. 23, 2013, the entirety of which is incorporated by reference herein. Also, the Sequence Listing filed electronically herewith is hereby incorporated by reference (File name: 2014-04-23T_US-495 Seq List; File size: 21 KB; Date recorded: Apr. 23, 2014).

BACKGROUND OF THE INVENTION

1. Field of the Invention

The present invention relates to the microbiological industry, and specifically to a method for producing L-amino acids by fermentation of a bacterium of the family Enterobacteriaceae which has been modified to attenuate expression of the yjjK gene.

2. Description of the Related Art

Conventionally, L-amino acids are industrially produced by fermentation methods utilizing strains of microorganisms obtained from natural sources, or mutants thereof. Typically, the microorganisms are modified to enhance production yields of L-amino acids.

Many techniques to enhance L-amino acid production yields have been reported, including transformation of microorganisms with recombinant DNA (see, for example, U.S. Pat. No. 4,278,765 A) and alteration of regulatory regions such as promoter, leader sequence, and/or attenuator, or others known to the person skilled in the art (see, for example, US20060216796 A1 and WO9615246 A1). Other techniques for enhancing production yields include increasing the activities of enzymes involved in amino acid biosynthesis and/or desensitizing the target enzymes to the feedback inhibition by the resulting L-amino acid (see, for example, WO9516042 A1, EP0685555 A1 or U.S. Pat. Nos. 4,346,170 A, 5,661,012 A, and 6,040,160 A).

Another method for enhancing L-amino acids production yields is to attenuate expression of a gene or several genes which are involved in degradation of the target L-amino acid, genes which divert the precursors of the target L-amino acid from the L-amino acid biosynthetic pathway, genes involved in the redistribution of the carbon, nitrogen, and phosphate fluxes, and genes encoding toxins, etc.

The yjjK gene product has been identified using two-dimensional gel electrophoresis (Link A. J. et al., Comparing the predicted and observed properties of proteins encoded in the genome of *Escherichia coli* K-12, *Electrophoresis*, 1997, 18(8):1259-1313). The YjjK protein was characterized later as a putative ABC transporter (ATP binding cassette), a member of one of the largest protein families known. ABC transporters have the common distinctive architecture, which consists of two transmembrane domains (TMDs) embedded in the membrane bilayer and two nucleotide-binding domains (NBDs) located in the cytoplasm (Rees D. C. et al., ABC transporters: the power to change, *Nat. Rev. Mol. Cell Biol.*, 2009, 10(3): 218-227). The prokaryotic ABC transporters can recruit a binding protein to translocate substrates. ATP binding to the nucleotide-binding domains and hydrolysis drive the conformational changes that result in translocation of a substrate. Functioning as importers or exporters, ABC transporters can transport a wide variety of substrates which include ions, toxins, antibiotics, lipids, polysaccharides, nutrients such as amino acids, peptides, sugars, and so forth. Little is known about function of the YjjK protein (Linton K. J. and Higgins C. F., The *Escherichia coli* ATP-binding cassette (ABC) proteins, *Mol. Microbiol.*, 1998, 28(1):5-13). It is only predicted by the sequence similarity approach that this protein is the ATP-binding component of a member of the ABC superfamily, subfamily 3 of transporters having the NBD-NBD domain organization.

Until now, no data has been reported demonstrating the effect from attenuating the yjjK gene on L-amino acid production by the modified bacterial strains of the family Enterobacteriaceae.

SUMMARY OF THE INVENTION

An aspect of the present invention is to provide a bacterium belonging to the family Enterobacteriaceae, which can belong to the genus *Escherichia* and, more specifically, to the species *Escherichia coli* (*E. coli*), which has been modified to attenuate expression of the yjjK gene.

Another aspect of the present invention is to provide a method for producing L-amino acids such as L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine using a bacterium of the family Enterobacteriaceae as described hereinafter.

These aims were achieved by the unexpected finding that attenuation of expression of the yjjK gene, in particular inactivation of the yjjK gene, on the chromosome of a bacterium belonging to the family Enterobacteriaceae, which can belong to the genus *Escherichia* and, more specifically, to the species *Escherichia coli*, confers on the microorganism higher productivity of L-amino acids, in particular, but are not limited to L-valine and L-histidine.

An aspect of the present invention is to provide a method for producing an L-amino acid comprising:

(i) cultivating the bacterium of the family Enterobacteriaceae in a culture medium to produce said L-amino acid in the bacterium and/or the culture medium; and (ii) collecting said L-amino acid from the bacterium and/or the culture medium, wherein the bacterium has been modified to attenuate expression of the yjjK gene.

It is a further aspect of the present invention to provide the method as described above, wherein the bacterium belongs to the genus *Escherichia*.

It is a further aspect of the present invention to provide the method as described above, wherein the bacterium belongs to the species *Escherichia coli*.

It is a further aspect of the present invention to provide the method as described above, wherein the bacterium belongs to the genus *Pantoea*.

It is a further aspect of the present invention to provide the method as described above, wherein the bacterium belongs to the species *Pantoea ananatis*.

It is a further aspect of the present invention to provide the method as described above, wherein the expression is attenuated due to inactivation of the yjjK gene.

It is a further aspect of the present invention to provide the method as described above, wherein the gene is deleted.

It is a further aspect of the present invention to provide the method as described above, wherein the yjjK gene is encoded by the nucleotide sequence of SEQ ID NO: 1 or a variant nucleotide sequence of SEQ ID NO: 1.

It is a further aspect of the present invention to provide the method as described above, wherein the L-amino acid is selected from the group consisting of an aromatic L-amino acid and a non-aromatic L-amino acid.

It is a further aspect of the present invention to provide the method as described above, wherein the aromatic L-amino acid is selected from the group consisting of L-phenylalanine, L-tryptophan, and L-tyrosine.

It is a further aspect of the present invention to provide the method as described above, wherein the non-aromatic L-amino acid is selected from the group consisting of L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-proline, L-serine, L-threonine, and L-valine.

DESCRIPTION OF THE PREFERRED EMBODIMENTS

The present invention is described in detail below.

1. Bacterium

The phrase "an L-amino acid-producing bacterium" can mean a bacterium of the family Enterobacteriaceae which has an ability to produce, excrete or secrete, and/or cause accumulation of an L-amino acid in a culture medium or the bacterial cells when the bacterium is cultured in the medium.

The phrase "an L-amino acid-producing bacterium" can also mean a bacterium which is able to produce, excrete or secrete, and/or cause accumulation of an L-amino acid in a culture medium in an amount larger than a wild-type or parental strain, such as E. coli K-12, and can mean that the microorganism is able to cause accumulation in a medium of an amount not less than 0.5 g/L or not less than 1.0 g/L of the target L-amino acid. The bacterium can produce an amino acid either alone or as a mixture of two or more kinds of amino acids.

The phrase "L-amino acid-producing ability" can mean the ability of the bacterium to produce, excrete or secrete, and/or cause accumulation of the L-amino acid in a medium or the bacterial cells to such a level that the L-amino acid can be collected from the medium or the bacterial cells, when the bacterium is cultured in the medium.

The phrase "L-amino acid" can mean L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine.

The phrase "aromatic L-amino acid" includes, for example, L-phenylalanine, L-tryptophan, and L-tyrosine.

The phrase "non-aromatic L-amino acid" includes, for example, L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-proline, L-serine, L-threonine, and L-valine.

An L-amino acid can belong to one or more L-amino acid families. As an example, the L-amino acid can belong to the glutamate family including L-arginine, L-glutamic acid, L-glutamine, and L-proline; the serine family including L-cysteine, glycine, and L-serine; the aspartate family including L-asparagine, L-aspartic acid, L-isoleucine, L-lysine, L-methionine, and L-threonine; the pyruvate family including L-alanine, L-isoleucine, L-valine, and L-leucine; and the aromatic family including L-phenylalanine, L-tryptophan, and L-tyrosine.

L-Arginine, L-cysteine, L-glutamic acid, L-histidine, L-leucine, L-lysine, L-phenylalanine, L-proline, L-threonine, L-tryptophan, and L-valine are particular examples. L-Histidine and L-valine are preferable examples.

The bacteria belonging to the family Enterobacteriaceae can be from the genera Enterobacter, Erwinia, Escherichia, Klebsiella, Morganella, Pantoea, Photorhabdus, Providencia, Salmonella, Yersinia, and so forth, and can have the ability to produce an L-amino acid. Specifically, those classified into the family Enterobacteriaceae according to the taxonomy used in the NCBI (National Center for Biotechnology Information) database (ncbi.nlm.nih.gov/Taxonomy/Browser/wwwtax.cgi?id=543) can be used. Examples of strains from the family Enterobacteriaceae which can be modified include a bacterium of the genus Escherichia, Enterobacter or Pantoea.

Strains of Escherichia bacterium which can be modified to obtain Escherichia bacteria in accordance with the presently disclosed subject matter are not particularly limited, and specifically, those described in the work of Neidhardt et al. can be used (Bachmann, B.J., Derivations and genotypes of some mutant derivatives of E. coli K-12, p. 2460-2488. In F.C. Neidhardt et al. (ed.), E. coli and Salmonella: cellular and molecular biology, $2^{nd}$ ed. ASM Press, Washington, D.C., 1996). The species E. coli is a particular example. Specific examples of E. coli include E. coli W3110 (ATCC 27325), E. coli MG1655 (ATCC 47076), and so forth, which are derived from the prototype wild-type strain, E. coli K-12 strain. These strains are available from, for example, the American Type Culture Collection (P.O. Box 1549, Manassas, Va. 20108, United States of America). That is, registration numbers are given to each of the strains, and the strains can be ordered by using these registration numbers (refer to atcc.org). The registration numbers of the strains are listed in the catalogue of the American Type Culture Collection.

Examples of the Enterobacter bacteria include Enterobacter agglomerans, Enterobacter aerogenes, and so forth. Examples of the Pantoea bacteria include Pantoea ananatis, and so forth. Some strains of Enterobacter agglomerans were recently reclassified into Pantoea agglomerans, Pantoea ananatis or Pantoea stewartii on the basis of nucleotide sequence analysis of 16S rRNA, etc. A bacterium belonging to any of the genus Enterobacter or Pantoea may be used so long as it is a bacterium classified into the family Enterobacteriaceae. When a Pantoea ananatis strain is bred by genetic engineering techniques, Pantoea ananatis AJ13355 strain (FERM BP-6614), AJ13356 strain (FERM BP-6615), AJ13601 strain (FERM BP-7207) and derivatives thereof can be used. These strains were identified as Enterobacter agglomerans when they were isolated, and deposited as Enterobacter agglomerans. However, they were recently re-classified as Pantoea ananatis on the basis of nucleotide sequencing of 16S rRNA and so forth as described above.

L-amino Acid-producing Bacteria

The bacterium of the present invention belonging to the family Enterobacteriaceae and modified to attenuate expression of the yjjK gene, which is able to produce either an aromatic or a non-aromatic L-amino acid, can be used.

The bacterium may inherently have the L-amino acid-producing ability or may be modified to have an L-amino acid-producing ability by using a mutation method or DNA recombination techniques. The bacterium can be obtained by attenuating expression of the yjjK gene in a bacterium which inherently has the ability to produce L-amino acids. Alternatively, the bacterium can be obtained by imparting the ability to produce L-amino acids to a bacterium already having the attenuated expression of the yjjK gene.

L-arginine-producing Bacteria

Examples of parental strains which can be used to derive L-arginine-producing bacteria include, but are not limited to strains belonging to the genus *Escherichia* such as *E. coli* strain 237 (VKPM B-7925) (U.S. Patent Application 2002/058315 A1) and its derivative strains harboring mutant N-acetylglutamate synthase (RU2215783), *E. coli* strain 382 (VKPM B-7926) (EP1170358 A1), an arginine-producing strain into which argA gene encoding N-acetylglutamate synthetase is introduced therein (EP1170361 A1), and the like.

Examples of parental strains which can be used to derive L-arginine-producing bacteria also include strains in which expression of one or more genes encoding an L-arginine biosynthetic enzyme are enhanced. Examples of such genes include genes encoding N-acetyl-γ-glutamylphosphate reductase (argC), ornithine acetyltransferase (argJ), N-acetylglutamate kinase (argB), N-acetylornithine aminotransferase (argD), ornithine carbamoyltransferase (argF), argininosuccinate synthase (argG), argininosuccinate lyase (argH), and carbamoyl phosphate synthetase (carAB).

L-citrulline-producing Bacteria

Examples of parental strains which can be used to derive L-citrulline-producing bacteria include, but are not limited to strains belonging to the genus *Escherichia* such as *E. coli* mutant N-acetylglutamate synthase strains 237/pMADS 11, 237/pMADS 12, and 237/pMADS 13 (RU2215783 C2, EP1170361 B1, U.S. Pat. No. 6,790,647 B2), *E. coli* strains 333 (VKPM B-8084) and 374 (VKPM B-8086), both harboring mutant feedback-resistant carbamoyl phosphate synthetase (Russian Patent RU2264459 C2), strains *E. coli*, in which α-ketoglutarate synthase activity is increased, and ferredoxin NADP$^+$ reductase, pyruvate synthase or α-ketoglutarate dehydrogenase activities are additionally modified (EP2133417 A1), and strain *P. ananantis* NA1sucAsdhA, in which succinate dehydrogenase and α-ketoglutarate dehydrogenase activities are decreased (US Patent Application No 2009286290), and the like.

As L-citrulline is an intermediate of L-arginine biosynthetic pathway, examples of parent strains, which can be used to derive L-citrulline-producing bacteria, include strains, in which expression of one or more genes encoding an L-arginine biosynthetic enzyme is enhanced. Examples of such genes include, but are not limited to, genes encoding N-acetylglutamate synthase (argA), N-acetylglutamate kinase (argB), N-acetylglutamyl phosphate reductase (argC), acetylornithine transaminase (argD), acetylornithine deacetylase (argE), ornithine carbamoyltransferase (argF/I), and carbamoyl phosphate synthetase (carAB), or combinations thereof.

L-citrulline-producing bacterium can be also easily obtained from any L-arginine-producing bacterium, for example *E. coli* 382 stain (VKPM B-7926), by inactivation of argininosuccinate synthase encoded by argG gene.

L-cysteine-producing Bacteria

Examples of parental strains which can be used to derive L-cysteine-producing bacteria include, but are not limited to strains belonging to the genus *Escherichia* such as *E. coli* JM15 which is transformed with different cysE alleles encoding feedback-resistant serine acetyltransferases (U.S. Pat. No. 6,218,168, Russian Patent No. 2279477), *E. coli* W3110 having overexpressed genes which encode proteins suitable for secreting substances toxic for cells (U.S. Pat. No. 5,972,663), *E. coli* strains having lowered cysteine desulfhydrase activity (JP11155571 A2), *E. coli* W3110 with increased activity of a positive transcriptional regulator for cysteine regulon encoded by the cysB gene (WO0127307 A1), *E. coli* JM15(ydeD) (U.S. Pat. No. 6,218,168), and the like.

L-glutamic Acid-producing Bacteria

Examples of parental strains which can be used to derive L-glutamic acid-producing bacteria include, but are not limited to strains belonging to the genus *Escherichia* such as *E. coli* VL334thrC$^+$ (EP 1172433). The *E. coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 grown on the wild-type *E. coli* strain K12 (VKPM B-7) cells. As a result, an L-isoleucine auxotrophic strain VL334thrC$^+$ (VKPM B-8961), which is able to produce L-glutamic acid, was obtained.

Examples of parental strains which can be used to derive the L-glutamic acid-producing bacteria include, but are not limited to strains in which expression of one or more genes encoding an L-glutamic acid biosynthetic enzyme are enhanced. Examples of such genes include genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phosphate dehydrogenase (gapA), triose phosphate isomerase (tpiA), fructose bisphosphate aldolase (fbp), phosphofructokinase (pfkA, pfkB), and glucose phosphate isomerase (pgi).

Examples of strains modified so that expression of the citrate synthetase gene, the phosphoenolpyruvate carboxylase gene, and/or the glutamate dehydrogenase gene is/are enhanced include those disclosed in EP1078989 A2, EP955368 A2, and EP952221 A2.

Examples of parental strains which can be used to derive the L-glutamic acid-producing bacteria also include strains having decreased or eliminated activity of an enzyme that catalyzes synthesis of a compound other than L-glutamic acid by branching off from an L-glutamic acid biosynthesis pathway. Examples of such enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), and glutamate decarboxylase (gadAB). Bacteria belonging to the genus *Escherichia* deficient in the α-ketoglutarate dehydrogenase activity or having a reduced α-ketoglutarate dehydrogenase activity and methods for obtaining them are described in U.S. Pat. Nos. 5,378,616 and 5,573,945. Specifically, these strains include the following:

*E. coli* W3110sucA::Km$^R$
*E. coli* AJ12624 (FERM BP-3853)
*E. coli* AJ12628 (FERM BP-3854)
*E. coli* AJ12949 (FERM BP-4881)

*E. coli* W3110sucA::Km$^R$ is a strain obtained by disrupting the α-ketoglutarate dehydrogenase gene (hereinafter referred to as "sucA gene") of *E. coli* W3110. This strain is completely deficient in α-ketoglutarate dehydrogenase.

Other examples of L-glutamic acid-producing bacterium include those which belong to the genus *Escherichia* and have resistance to an aspartic acid antimetabolite. These strains can also be deficient in the α-ketoglutarate dehydrogenase activity and include, for example, *E. coli* AJ13199 (FERM BP-5807) (U.S. Pat. No. 5,908,768), FFRM P-12379, which additionally has a low L-glutamic acid decomposing ability (U.S. Pat. No. 5,393,671), AJ13138 (FERM BP-5565) (U.S. Pat. No. 6,110,714), and the like.

Examples of L-glutamic acid-producing bacteria include mutant strains belonging to the genus *Pantoea* which are deficient in the α-ketoglutarate dehydrogenase activity or have a decreased α-ketoglutarate dehydrogenase activity, and can be obtained as described above. Such strains include *Pantoea ananatis* AJ13356. (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, Incorporated Administrative Agency, National Institute of Technology and Evaluation, International Patent Organism (NITE IPOD), #120, 2-5-8 Kazusakamatari, Kisarazu-shi, Chiba-ken 292-0818, JAPAN) on Feb. 19, 1998 under an accession number of FERM P-16645. It was then converted to an international deposit under the provisions of Budapest Treaty on Jan. 11, 1999 and received an accession number of FERM BP-6615. *Pantoea ananatis* AJ13356 is deficient in α-ketoglutarate dehydrogenase activity as a result of disruption of the αKGDH-E1 subunit gene (sucA). The above strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *Pantoea ananatis*.

L-histidine-producing Bacteria

Examples of parental strains which can be used to derive L-histidine-producing bacteria include, but are not limited to strains belonging to the genus *Escherichia* such as *E. coli* strain 24 (VKPM B-5945, RU2003677 C1), *E. coli* strain 80 (VKPM B-7270, RU2119536 C1), *E. coli* NRRL B-12116-B12121 (U.S. Pat. No. 4,388,405), *E. coli* H-9342 (FERM BP-6675) and H-9343 (FERM BP-6676) (U.S. Pat. No. 6,344,347), *E. coli* H-9341 (FERM BP-6674) (EP1085087), *E. coli* AI80/pFM201 (U.S. Pat. No. 6,258,554), and the like.

Examples of parental strains which can be used to derive L-histidine-producing bacteria also include strains in which expression of one or more genes encoding an L-histidine biosynthetic enzyme are enhanced. Examples of such genes include genes encoding ATP phosphoribosyltransferase (hisG), phosphoribosyl-AMP cyclohydrolase (hisI), phosphoribosyl-AMP cyclohydrolase/phosphoribosyl-ATP pyrophosphatase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine, and therefore an L-histidine-producing ability can also be efficiently enhanced by introducing a mutation conferring resistance to the feedback inhibition into ATP phosphoribosyltransferase (Russian Patent Nos. 2003677 and 2119536).

Specific examples of strains having an L-histidine-producing ability include *E. coli* FERM-P 5038 and 5048 which have been transformed with a vector carrying a DNA encoding an L-histidine-biosynthetic enzyme (JP 56-005099 A), *E. coli* strains transformed with rht, a gene for an amino acid-export (EP1016710 A), *E. coli* 80 strain imparted with sulfaguanidine, DL-1,2,4-triazole-3-alanine, and streptomycin-resistance (VKPM B-7270, RU2119536), and *E. coli* MG1655+ hisGr hisL'_Δ ΔpurR (RU2119536 C1; Doroshenko V. G. et al., The directed modification of *Escherichia coli* MG1655 to obtain histidine-producing mutants, *Prikl. Biochim. Mikrobiol.* (*Russian*), 2013, 49(2):149-154), and so forth.

L-isoleucine-producing Bacteria

Examples of parental strains which can be used to derive L-isoleucine-producing bacteria include, but are not limited to mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as parental strains (JP 2-458 A, EP0356739 A1, and U.S. Pat. No. 5,998,178).

L-leucine-producing Bacteria

Examples of parental strains which can be used to derive L-leucine-producing bacteria include, but are not limited to strains belonging to the genus *Escherichia* such as *E. coli* strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5,5-trifluoroleucine (JP 62-34397 B and JP 8-70879 A); *E. coli* strains obtained by the gene engineering method described in WO96/06926; *E. coli* H-9068 (JP 8-70879 A), and the like.

The bacterium can be improved by enhancing the expression of one or more genes involved in L-leucine biosynthesis. Examples include genes of the leuABCD operon, which can be represented by a mutant leuA gene encoding isopropylmalate synthase freed from feedback inhibition by L-leucine (U.S. Pat. No. 6,403,342). In addition, the bacterium can be improved by enhancing the expression of one or more genes encoding proteins which excrete L-amino acid from the bacterial cell. Examples of such genes include the b2682 and b2683 genes (ygaZH genes) (EP1239041 A2).

L-lysine-producing Bacteria

Examples of L-lysine-producing bacteria belonging to the family *Escherichia* include mutants having resistance to an L-lysine analogue. The L-lysine analogue inhibits growth of bacteria belonging to the genus *Escherichia*, but this inhibition is fully or partially desensitized when L-lysine is present in the medium. Examples of the L-lysine analogue include, but are not limited to oxalysine, lysine hydroxamate, S-(2-aminoethyl)-L-cysteine (AEC), γ-methyllysine, α-chlorocaprolactam, and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *E. coli* AJ11442 (FERM BP-1543, NRRL B-12185; see U.S. Pat. No. 4,346, 170) and *E. coli* VL611. In these microorganisms, feedback inhibition of aspartokinase by L-lysine is desensitized.

Examples of parental strains which can be used to derive L-lysine-producing bacteria also include strains in which expression of one or more genes encoding an L-lysine biosynthetic enzyme are enhanced. Examples of such genes include, but are not limited to genes encoding dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyruvate carboxylase (ppc), aspartate semialdehyde dehydrogenease (asd), and aspartase (aspA) (EP1253195 A1). In addition, the parental strains may have an increased level of expression of the gene involved in energy efficiency (cyo) (EP1170376 A1), the gene encoding nicotinamide nucleotide transhydrogenase (pntAB) (U.S. Pat. No. 5,830,716), the ybjE gene (WO2005/073390), or combinations thereof.

L-Amino acid-producing bacteria may have reduced or no activity of an enzyme that catalyzes a reaction which causes a branching off from the L-amino acid biosynthesis pathway and results in the production of another compound. Also, the bacteria may have reduced or no activity of an enzyme that negatively acts on L-amino acid synthesis or accumulation. Examples of such enzymes involved in L-lysine production include homoserine dehydrogenase, lysine decarboxylase (cadA, ldcC), malic enzyme, and so forth, and strains in which activities of these enzymes are decreased or deleted are disclosed in WO95/23864, WO96/17930, WO2005/010175, and so forth.

Expression of both the cadA and ldcC genes encoding lysine decarboxylase can be decreased in order to decrease or delete the lysine decarboxylase activity. Expression of the both genes can be decreased by, for example, the method described in WO2006/078039.

Examples of L-lysine-producing bacteria can include the *E. coli* WC196ΔcadAΔldcC/pCABD2 strain (WO2006/078039). The strain was constructed by introducing the plasmid pCABD2 containing lysine biosynthesis genes (U.S. Pat. No. 6,040,160) into the WC196 strain having disrupted cadA and ldcC genes which encode lysine decarboxylase.

The WC196 strain was bred from the W3110 strain, which was derived from *E. coli* K-12 by replacing the wild-type lysC gene on the chromosome of the W3110 strain with a mutant lysC gene encoding a mutant aspartokinase III in which threonine at position 352 was replaced with isoleucine, resulting in desensitization of the feedback inhibition by L-lysine (U.S. Pat. No. 5,661,012), and conferring AEC resistance to the resulting strain (U.S. Pat. No. 5,827,698). The WC196 strain was designated *E. coli* AJ13069, deposited at the National Institute of Bioscience and Human-Technology, Agency of Industrial Science and Technology (currently Incorporated Administrative Agency, National Institute of Technology and Evaluation, International Patent Organism (NITE IPOD), #120, 2-5-8 Kazusakamatari, Kisarazu-shi, Chiba-ken 292-0818, JAPAN) on Dec. 6, 1994, and assigned an accession number of FERM P-14690. Then, it was converted to an international deposit under the provisions of the Budapest Treaty on Sep. 29, 1995, and assigned an accession number of FERM BP-5252 (U.S. Pat. No. 5,827,698).

The WC196ΔcadAΔldcC strain itself is also an exemplary L-lysine-producing bacterium. The WC196ΔcadAΔldcC was designated AJ110692 and deposited at the National Institute of Bioscience and Human-Technology, Agency of Industrial Science and Technology (currently Incorporated Administrative Agency, National Institute of Technology and Evaluation, International Patent Organism (NITE IPOD), #120, 2-5-8 Kazusakamatari, Kisarazu-shi, Chiba-ken 292-0818, JAPAN) on Oct. 7, 2008 as an international deposit under an accession number of FERM BP-11027.

L-methionine-producing Bacteria

Examples of L-methionine-producing bacteria and parent strains which can be used to derive L-methionine-producing bacteria include, but are not limited to *Escherichia* bacteria strains such as strains AJ11539 (NRRL B-12399), AJ11540 (NRRL B-12400), AJ11541 (NRRL B-12401), AJ 11542 (NRRL B-12402) (GB Patent GB2075055); strains 218 (VKPM B-8125) (Russian patent RU2209248 C2) and 73 (VKPM B-8126) (Russian patent RU2215782 C2) resistant to norleucine, the L-methionine analog, or the like. The strain *E. coli* 73 has been deposited in the Russian National Collection of Industrial Microorganisms (VKPM) (Russian Federation, 117545 Moscow, 1$^{st}$ Dorozhny proezd, 1) on May 14, 2001 under accession number VKPM B-8126, and was converted to an international deposit under the Budapest Treaty on Feb. 1, 2002. Furthermore, a methionine repressor-deficient strain and recombinant strains transformed with genes encoding proteins involved in L-methionine biosynthesis such as homoserine transsuccinylase and cystathionine γ-synthase (JP 2000-139471 A) can also be used as parent strains.

L-ornithine-producing Bacteria

L-ornithine-producing bacterium can be easily obtained from any L-arginine-producing bacterium, for example *E. coli* 382 stain (VKPM B-7926), by inactivation of ornithine carbamoyltransferase encoded by both argF and argI genes. Methods for inactivation of ornithine carbamoyltransferase are described herein.

L-phenylalanine-producing Bacteria

Examples of parental strains which can be used to derive L-phenylalanine-producing bacteria include, but are not limited to strains belonging to the genus *Escherichia* such as *E. coli* AJ12739 (tyrA::Tn10, tyrR) (VKPM B-8197), *E. coli* HW1089 (ATCC 55371) harboring the mutant pheA34 gene (U.S. Pat. No. 5,354,672), *E. coli* MWEC101-b (KR8903681), *E. coli* NRRL B-12141, NRRL B-12145, NRRL B-12146 and NRRL B-12147 (U.S. Pat. No. 4,407,952). Also, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662), and *E. coli* K-12 [W3110 (tyrA)/pBR-aroG4, pACMAB] named as AJ 12604 (FERM BP-3579) may be used as a parental strain (EP488424 B1). Furthermore, L-phenylalanine-producing bacteria belonging to the genus *Escherichia* with an enhanced activity of the protein encoded by the yedA gene or the yddG gene may also be used (U.S. patent applications 2003/0148473 A1 and 2003/0157667 A1).

L-proline-producing Bacteria

Examples of parental strains which can be used to derive L-proline-producing bacteria include, but are not limited to strains belonging to the genus *Escherichia* such as *E. coli* 702ilvA (VKPM B-8012) which is deficient in the ilvA gene and is able to produce L-proline (EP1172433 A1). The bacterium can be improved by enhancing the expression of one or more genes involved in L-proline biosynthesis. Examples of genes which can be used in L-proline-producing bacteria include the proB gene encoding glutamate kinase with desensitized feedback inhibition by L-proline (DE3127361 A1). In addition, the bacterium can be improved by enhancing the expression of one or more genes encoding proteins excreting L-amino acid from bacterial cell. Such genes are exemplified by b2682 and b2683 genes (ygaZH genes) (EP1239041 A2).

Examples of bacteria belonging to the genus *Escherichia*, which have an activity to produce L-proline include the following *E. coli* strains: NRRL B-12403 and NRRL B-12404 (GB Patent 2075056), VKPM B-8012 (Russian patent application No. 2000124295), plasmid mutants described in DE3127361 A1, plasmid mutants described by Bloom F. R. et al. in "The 15$^{th}$ Miami winter symposium", 1983, p. 34, and the like.

L-threonine-producing Bacteria

Examples of parental strains which can be used to derive L-threonine-producing bacteria include, but are not limited to strains belonging to the genus *Escherichia* such as *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520

(U.S. Pat. No. 5,376,538), *E. coli* MG442 (Gusyatiner et al., Genetika (Russian), 1978, 14:947-956), *E. coli* VL643 and VL2055 (EP1149911 A2), and the like.

The strain TDH-6 is deficient in the thrC gene, as well as being sucrose-assimilative, and the ilvA gene has a leaky mutation. This strain also has a mutation in the rhtA gene, which imparts resistance to high concentrations of threonine or homoserine. The strain B-3996 contains the plasmid pVIC40 which was obtained by inserting a thrA*BC operon which includes a mutant thrA gene into a RSF1010-derived vector. This mutant thrA gene encodes aspartokinase homoserine dehydrogenase I which has substantially desensitized feedback inhibition by threonine. The strain B-3996 was deposited on Nov. 19, 1987 in the All-Union Scientific Center of Antibiotics (Russian Federation, 117105 Moscow, Nagatinskaya Street 3-A) under the accession number RIA 1867. The strain was also deposited in the Russian National Collection of Industrial Microorganisms (VKPM) (Russian Federation, 117545 Moscow, 1$^{st}$ Dorozhny proezd, 1) on Apr. 7, 1987 under the accession number B-3996.

*E. coli* VKPM B-5318 (EP0593792 A1) may also be used as a parental strain for deriving L-threonine-producing bacteria. The strain B-5318 is prototrophic with regard to isoleucine; and a temperature-sensitive lambda-phage C1 repressor and PR promoter replace the regulatory region of the threonine operon in plasmid pVIC40. The strain VKPM B-5318 was deposited in the Russian National Collection of Industrial Microorganisms (VKPM) on May 3, 1990 under the accession number of VKPM B-5318.

The bacterium can be additionally modified to enhance expression of one or more of the following genes:
the mutant thrA gene which encodes aspartokinase homoserine dehydrogenase I resistant to feedback inhibition by threonine;
the thrB gene which encodes homoserine kinase;
the thrC gene which encodes threonine synthase;
the rhtA gene which encodes a putative transmembrane protein of the threonine and homoserine efflux system;
the asd gene which encodes aspartate-β-semialdehyde dehydrogenase; and
the aspC gene which encodes aspartate aminotransferase (aspartate transaminase);

The thrA gene which encodes aspartokinase I and homoserine dehydrogenase I of *E. coli* has been elucidated (KEGG entry No. b0002; GenBank accession No. NC_000913.2; nucleotide positions: 337 to 2,799; Gene ID: 945803). The thrA gene is located between the thrL and thrB genes on the chromosome of *E. coli* K-12.

The thrB gene which encodes homoserine kinase of *E. coli* has been elucidated (KEGG entry No. b0003; GenBank accession No. NC_000913.2; nucleotide positions: 2,801 to 3,733; Gene ID: 947498). The thrB gene is located between the thrA and thrC genes on the chromosome of *E. coli* K-12.

The thrC gene which encodes threonine synthase of *E. coli* has been elucidated (KEGG entry No. b0004; GenBank accession No. NC_000913.2; nucleotide positions: 3,734 to 5,020; Gene ID: 945198). The thrC gene is located between the thrB and yaaX genes on the chromosome of *E. coli* K-12. All three genes function as a single threonine operon thrABC. To enhance expression of the threonine operon, the attenuator region which affects the transcription is desirably removed from the operon (WO2005049808 A1, WO2003097839 A1).

The mutant thrA gene which encodes aspartokinase I and homoserine dehydrogenase I resistant to feedback inhibition by L-threonine, as well as, the thrB and thrC genes can be obtained as one operon from the well-known plasmid pVIC40 which is present in the L-threonine-producing *E. coli* strain VKPM B-3996. Plasmid pVIC40 is described in detail in U.S. Pat. No. 5,705,371.

The rhtA gene which encodes a protein of the threonine and homoserine efflux system (an inner membrane transporter) of *E. coli* has been elucidated (KEGG entry No. b0813; GenBank accession No. NC_000913.2; nucleotide positions: 848,433 to 849,320, complement; Gene ID: 947045). The rhtA gene is located between the dps and ompX genes on the chromosome of *E. coli* K-12 close to the glnHPQ operon, which encodes components of the glutamine transport system. The rhtA gene is identical to the ybiF gene (KEGG entry No. B0813).

The asd gene which encodes aspartate-β-semialdehyde dehydrogenase of *E. coli* has been elucidated (KEGG entry No. b3433; GenBank accession No. NC_000913.2; nucleotide positions: 3,571,798 to 3,572,901, complement; Gene ID: 947939). The asd gene is located between the glgB and gntU gene on the same strand (yhgN gene on the opposite strand) on the chromosome of *E. coli* K-12.

Also, the aspC gene which encodes aspartate aminotransferase of *E. coli* has been elucidated (KEGG entry No. b0928; GenBank accession No. NC_000913.2; nucleotide positions: 983,742 to 984,932, complement; Gene ID: 945553). The aspC gene is located between the ycbL gene on the opposite strand and the ompF gene on the same strand on the chromosome of *E. coli* K-12.

L-tryptophan-producing Bacteria

Examples of parental strains which can be used to derive the L-tryptophan-producing bacteria include, but are not limited to strains belonging to the genus *Escherichia* such as *E. coli* JP4735/pMU3028 (DSM10122) and JP6015/pMU91 (DSM10123) deficient in the tryptophanyl-tRNA synthetase encoded by mutant trpS gene (U.S. Pat. No. 5,756,345), *E. coli* SV164 (pGH5) having a serA allele encoding phosphoglycerate dehydrogenase free from feedback inhibition by serine and a trpE allele encoding anthranilate synthase free from feedback inhibition by tryptophan (U.S. Pat. No. 6,180,373), *E. coli* AGX17 (pGX44) (NRRL B-12263) and AGX6 (pGX50)aroP (NRRL B-12264) deficient in the enzyme tryptophanase (U.S. Pat. No. 4,371,614), *E. coli* AGX17/pGX50, pACKG4-pps in which a phosphoenolpyruvate-producing ability is enhanced (WO9708333, U.S. Pat. No. 6,319,696), and the like may be used. L-tryptophan-producing bacteria belonging to the genus *Escherichia* with an enhanced activity of the identified protein encoded by and the yedA gene or the yddG gene may also be used (U.S. patent applications 2003/0148473 A1 and 2003/0157667 A1).

Examples of parental strains which can be used to derive the L-tryptophan-producing bacteria also include strains in which one or more activities of the enzymes selected from anthranilate synthase, phosphoglycerate dehydrogenase, and tryptophan synthase are enhanced. The anthranilate synthase and phosphoglycerate dehydrogenase are both subject to feedback inhibition by L-tryptophan and L-serine, so that a mutation desensitizing the feedback inhibition may be introduced into these enzymes. Specific examples of strains having such a mutation include an *E. coli* SV164 which harbors desensitized anthranilate synthase and a transformant strain obtained by introducing into the *E. coli* SV164 the plasmid pGH5 (WO 94/08031), which contains a mutant serA gene encoding feedback-desensitized phosphoglycerate dehydrogenase.

Examples of parental strains which can be used to derive the L-tryptophan-producing bacteria also include strains into which the tryptophan operon which contains a gene encoding desensitized anthranilate synthase has been introduced (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). The tryptophan synthase consists of α and β subunits which are encoded by the trpA and trpB genes, respectively. In addition, L-tryptophan-producing ability may be improved by enhancing expression of the isocitrate lyase-malate synthase operon (WO2005/103275).

L-valine-producing Bacteria

Examples of parental strains which can be used to derive L-valine-producing bacteria include, but are not limited to strains which have been modified to overexpress the ilvGMEDA operon (U.S. Pat. No. 5,998,178). It is desirable to remove the region of the ilvGMEDA operon which is required for attenuation so that expression of the operon is not attenuated by the L-valine that is produced. Furthermore, the ilvA gene in the operon is desirably disrupted so that threonine deaminase activity is decreased.

Examples of parental strains for deriving L-valine-producing bacteria also include mutants having a mutation of aminoacyl-tRNA synthetase (U.S. Pat. No. 5,658,766). For example, E. coli VL1970, which has a mutation in the ileS gene encoding isoleucine tRNA synthetase, can be used. E. coli VL1970 was deposited in the Russian National Collection of Industrial Microorganisms (VKPM) (Russian Federation, 117545 Moscow, 1$^{st}$ Dorozhny Proezd, 1) on Jun. 24, 1988 under the accession number VKPM B-4411.

Furthermore, mutants requiring lipoic acid for growth and/or lacking H$^+$-ATPase can also be used as parental strains (WO96/06926).

Examples of L-valine-producing strain include E. coli strain H-81 (VKPM B-8066), NRRL B-12287 and NRRL B-12288 (U.S. Pat. No. 4,391,907), VKPM B-4411 (U.S. Pat. No. 5,658,766), VKPM B-7707 (European patent application EP1016710 A2), or the like.

The bacterium of the present invention belonging to the family Enterobacteriaceae has been modified to attenuate expression of the yjjK gene.

The phrase "a bacterium modified to attenuate expression of the yjjK gene" can mean that the bacterium has been modified in such a way that in the modified bacterium, expression of the yjjK gene is decreased as compared to a bacterium which contains a non-modified yjjK gene, for example, a wild-type or parental strain, or the yjjK gene is inactivated.

The phrase "the yjjK gene is inactivated" can mean that the modified gene encodes a completely inactive or non-functional protein. It is also possible that the modified DNA region is unable to naturally express the gene due to deletion of a part of the gene or deletion of the entire gene, replacement of one base or more to cause an amino acid substitution in the protein encoded by the gene (missense mutation), introduction of a stop codon (nonsense mutation), deletion of one or two bases to cause a reading frame shift of the gene, insertion of a drug-resistance gene and/or transcription termination signal, or modification of an adjacent region of the gene, including sequences controlling gene expression such as promoter(s), enhancer(s), attenuator(s), ribosome-binding site(s) (RBS), etc. Inactivation of the gene can also be performed, for example, by conventional methods such as a mutagenesis treatment using UV irradiation or nitrosoguanidine (N-methyl-N'-nitro-N-nitrosoguanidine), site-directed mutagenesis, gene disruption using homologous recombination, and/or insertion-deletion mutagenesis (Yu D. et al., *Proc. Natl. Acad. Sci. USA*, 2000, 97(11):5978-5983; Datsenko K. A. and Wanner B. L., *Proc. Natl. Acad. Sci. USA*, 2000, 97(12):6640-6645; Zhang Y. et al., *Nature Genet.*, 1998, 20:123-128) based on "Red/ET-driven integration" or "λRed/ET-mediated integration".

The phrase "expression of the yjjK gene is attenuated" can mean that an amount of the YjjK protein in the modified bacterium, in which expression of the yjjK gene is attenuated, is reduced as compared with a non-modified bacterium, for example, a wild-type or parental strain such as E. coli K-12.

The phrase "expression of the yjjK gene is attenuated" can also mean that the modified bacterium contains a region operably linked to the gene, including sequences controlling gene expression such as promoters, enhancers, attenuators and transcription termination signals, ribosome-binding sites (RBS), and other expression control elements, which is modified resulting in a decrease in the expression level of the yjjK gene; and other examples (see, for example, WO95/34672; Carrier T. A. and Keasling J. D., *Biotechnol. Prog.*, 1999, 15:58-64).

Expression of the yjjK gene can be attenuated by replacing an expression control sequence of the gene, such as a promoter on the chromosomal DNA, with a weaker one. The strength of a promoter is defined by the frequency of initiation acts of RNA synthesis. Examples of methods for evaluating the strength of promoters and strong promoters are described in Goldstein et al., Prokaryotic promoters in biotechnology, *Biotechnol. Annu. Rev.*, 1995, 1:105-128), and so forth. Furthermore, it is also possible to introduce nucleotide substitution for several nucleotides in a promoter region of a target gene and thereby modify the promoter to be weakened as disclosed in International Patent Publication WO00/18935. Furthermore, it is known that substitution of several nucleotides in the Shine-Dalgarno (SD) sequence, and/or in the spacer between the SD sequence and the start codon, and/or a sequence immediately upstream and/or downstream from the start codon in the ribosome-binding site (RBS) greatly affects the translation efficiency of mRNA. This modification of the RBS may be combined with decreasing transcription of the yjjK gene.

Expression of the yjjK gene can also be attenuated by insertion of a transposon or an insertion sequence (IS) into the coding region of the gene (U.S. Pat. No. 5,175,107) or in the region controlling gene expression, or in the proximal part of the yjjK gene structure, where the yjjK is the distal part, or by conventional methods such as mutagenesis with ultraviolet irradiation (UV) irradiation or nitrosoguanidine (N-methyl-N'-nitro-N-nitrosoguanidine). Furthermore, the incorporation of a site-specific mutation can be conducted by known chromosomal editing methods based, for example, on λRed/ET-mediated recombination.

The copy number, presence or absence of the gene can be measured, for example, by restricting the chromosomal DNA followed by Southern blotting using a probe based on the gene sequence, fluorescence in situ hybridization (FISH), and the like. The level of gene expression can be determined by measuring the amount of mRNA transcribed from the gene using various well-known methods, including Northern blotting, quantitative RT-PCR, and the like. The amount of the protein encoded by the gene can be measured by known methods including SDS-PAGE followed by immunoblotting assay (Western blotting analysis), or mass spectrometry analysis of the protein samples, and the like.

Methods for manipulation with recombinant molecules of DNA and molecular cloning such as preparation of plasmid DNA, digestion, ligation and transformation of DNA, selection of an oligonucleotide as a primer, incorporation of mutations, and the like may be ordinary methods well-known to the person skilled in the art. These methods are described, for example, in Sambrook J., Fritsch E. F. and Maniatis T., "Molecular Cloning: A Laboratory Manual", 2nd ed., Cold Spring Harbor Laboratory Press (1989) or Green M. R. and Sambrook J. R., "Molecular Cloning: A Laboratory Manual", 4th ed., Cold Spring Harbor Laboratory Press (2012); Bernard R. Glick, Jack J. Pasternak and Cheryl L. Patten, "Molecular Biotechnology: principles and applications of recombinant DNA", 4th ed., Washington, D.C., ASM Press (2009).

The yjjK gene encodes the fused predicted transporter subunits of ABC superfamily, ATP-binding components YjjK (KEGG, Kyoto Encyclopedia of Genes and Genomes, entry No. b4391; Protein Knowledgebase, UniProtKB/Swiss-Prot, accession No. P0A9W3). The yjjK gene (GenBank accession No. NC_000913.2; nucleotide positions: 4626878 to 4628545, complement; Gene ID: 948909) is located between the nadR and slt genes on the opposite strand on the chromosome of *E. coli* strain K-12. The nucleotide sequence of the yjjK gene and the amino acid sequence of the YjjK protein encoded by the yjjK gene are shown in SEQ ID NO: 1 and SEQ ID NO: 2, respectively.

The amino acid sequences of the ABC transporter ATP-binding protein YjjK from other bacterial species belonging to the family Enterobacteriaceae are known. The exemplary YjjK proteins are listed, for example, in the Protein Knowledgebase, UniProtKB/Swiss-Prot (uniprot.org/) under accession Nos. F2EU25(*Pantoea ananatis*, strain AJ13355, FERM BP-6614), D0ZV61 (*Salmonella typhimurium*, strain 14028s / SGSC 2262, The Salmonella Genetic Stock Centre (SGSC), Department of Biological Sciences, 2500 University Dr. N.W. Calgary, Alberta, Canada T2N 1N4), P0A9W5 (*Shigella flexneri*) or a homolog thereof from *Shigella flexneri* Castellani and Chalmers, ATCC 29903, B2VH30 (*Erwinia tasmaniensis*, strain DSM 17950/Et1/99, Leibniz Institute, DSMZ-German Collection of Microorganisms and Cell Cultures, Inhoffenstrasse 7B, 38124 Braunschweig, Germany), C7BJV0 (*Photorhabdus asymbiotica* subsp. asymbiotica, strain ATCC 43949/3105-77), and so forth.

Since there may be some differences in DNA sequences between the genera, species or strains of the family Enterobacteriaceae, the yjjK gene is not limited to the gene shown in SEQ ID NO: 1, but may include genes which are variant nucleotide sequences of or homologous to SEQ ID NO: 1, and which encode variants of the YjjK protein.

The phrase "a variant protein" can mean a protein which has one or several changes in the sequence compared with SEQ ID NO: 2, whether they are substitutions, deletions, insertions, and/or additions of one or several amino acid residues, but still maintains an activity or function similar to that of the YjjK protein, or the three-dimensional structure of the YjjK protein is not significantly changed relative to the wild-type or non-modified protein. The number of changes in the variant protein depends on the position in the three-dimensional structure of the protein or the type of amino acid residues. It can be, but is not strictly limited to, 1 to 30, in another example 1 to 15, in another example 1 to 10, and in another example 1 to 5, in SEQ ID NO: 2. These changes in the variant protein can occur in regions of the protein that are not critical for the activity or function of the protein. This is because some amino acids have high homology to one another so that the activity or function is not affected by such a change, or the three-dimensional structure of YjjK is not significantly changed relative to the wild-type or non-modified protein. Therefore, the protein variants encoded by the yjjK gene may have a homology, defined as the parameter "identity" when using the computer program BLAST, of not less than 80%, not less than 90%, not less than 95%, or not less than 98% with respect to the entire amino acid sequence shown in SEQ ID NO: 2, as long as the activity or function of the YjjK protein is maintained, or the three-dimensional structure of YjjK is not significantly changed relative to the wild-type or non-modified protein.

The exemplary substitution, deletion, insertion, and/or addition of one or several amino acid residues can be a conservative mutation(s). The representative conservative mutation is a conservative substitution. The conservative substitution can be, but is not limited to a substitution, wherein substitution takes place mutually among Phe, Trp and Tyr, if the substitution site is an aromatic amino acid; among Ala, Leu, Ile and Val, if the substitution site is a hydrophobic amino acid; between Glu, Asp, Gln, Asn, Ser, His and Thr, if the substitution site is a hydrophilic amino acid; between Gln and Asn, if the substitution site is a polar amino acid; among Lys, Arg and His, if the substitution site is a basic amino acid; between Asp and Glu, if the substitution site is an acidic amino acid; and between Ser and Thr, if the substitution site is an amino acid having hydroxyl group. Examples of conservative substitutions include substitution of Ser or Thr for Ala, substitution of Gln, His or Lys for Arg, substitution of Glu, Gln, Lys, His or Asp for Asn, substitution Asn, Glu or Gln for Asp, substitution of Ser or Ala for Cys, substitution Asn, Glu, Lys, His, Asp or Arg for Gln, substitution Asn, Gln, Lys or Asp for Glu, substitution of Pro for Gly, substitution Asn, Lys, Gln, Arg or Tyr for His, substitution of Leu, Met, Val or Phe for Ile, substitution of Ile, Met, Val or Phe for Leu, substitution Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

The exemplary substitution, deletion, insertion, and/or addition of one or several amino acid residues can also be a non-conservative mutation(s) provided that the mutation(s) is/are compensated by one or more secondary mutations in the different position(s) of amino acids sequence so that the activity or function of the variant protein is maintained and similar to that of the YjjK protein, or the three-dimensional structure of YjjK is not significantly changed relative to the wild-type or non-modified protein.

To evaluate the degree of protein or DNA homology, several calculation methods can be used, such as BLAST search, FASTA search and ClustalW method. The BLAST (Basic Local Alignment Search Tool, ncbi.nlm.nih.gov/BLAST/) search is the heuristic search algorithm employed by the programs blastp, blastn, blastx, megablast, tblastn, and tblastx; these programs ascribe significance to their findings using the statistical methods of Samuel K. and Altschul S.F. ("Methods for assessing the statistical significance of molecular sequence features by using general scoring schemes" *Proc. Natl. Acad. Sci. USA*, 1990, 87:2264-2268; "Applications and statistics for multiple high-scoring segments in molecular sequences". *Proc. Natl. Acad. Sci. USA*, 1993, 90:5873-5877). The computer program BLAST calculates three parameters: score, identity and similarity. The FASTA search method is described by Pearson W.R. ("Rapid and sensitive sequence comparison with FASTP and FASTA", *Methods Enzymol.,* 1990, 183:63-98). The ClustalW method is described by Thompson J.D. et al. ("CLUSTAL W: improving the sensitivity of progressive multiple sequence alignment through sequence weighting, position-specific gap penalties and weight matrix choice", *Nucleic Acids Res.,* 1994, 22:4673-4680).

Moreover, the yjjK gene can be a variant nucleotide sequence. The phrase "a variant nucleotide sequence" can mean a nucleotide sequence which encodes the YjjK protein using any synonymous amino acid codons according to the standard genetic code table (see, e.g., Lewin B., "Genes VIII", 2004, Pearson Education, Inc., Upper Saddle River, N.J. 07458), or "a variant protein" of the YjjK protein. The yjjK gene can be a variant nucleotide sequence due to degeneracy of genetic code.

The phrase "a variant nucleotide sequence" can also mean, but is not limited to a nucleotide sequence which hybridizes under stringent conditions with the nucleotide sequence complementary to the sequence shown in SEQ ID NO: 1, or a probe which can be prepared from the nucleotide sequence under stringent conditions provided that it encodes functional protein. "Stringent conditions" include those under which a specific hybrid, for example, a hybrid having homology, defined as the parameter "identity" when using the computer program BLAST, of not less than 70%, not less than 80%, not less than 90%, not less than 95%, not less than 96%, not less than 97%, not less than 98%, or not less than 99% is formed, and a non-specific hybrid, for example, a hybrid having homology lower than the above is not formed. For example, stringent conditions can be exemplified by washing one time or more, or in another example, two or three times, at a salt concentration of 1×SSC (standard sodium citrate or standard sodium chloride), 0.1% SDS (sodium dodecyl sulphate), or in another example, 0.1×SSC, 0.1% SDS at 60° C. or 65° C. Duration of washing depends on the type of membrane used for blotting and, as a rule, can be what is recommended by the manufacturer. For example, the recommended duration of washing for the Amersham Hybond™-N+ positively charged nylon membrane (GE Healthcare) under stringent conditions is 15 minutes. The washing step can be performed 2 to 3 times. As the probe, a part of the sequence complementary to the sequences shown in SEQ ID NO: 1 may also be used. Such a probe can be produced by PCR using oligonucleotides as primers prepared on the basis of the sequence shown in SEQ ID NO: 1 and a DNA fragment containing the nucleotide sequence as a template. The length of the probe is recommended to be >50 bp; it can be suitably selected depending on the hybridization conditions, and is usually 100 bp to 1 kbp. For example, when a DNA fragment having a length of about 300 bp is used as the probe, the washing conditions after hybridization can be exemplified by 2×SSC, 0.1% SDS at 50° C., 60° C. or 65° C.

As the genes encoding the YjjK proteins of the genera *Escherichia, Pantoea, Shigella, Erwinia*, and *Photorhabdus* have already been elucidated (see above), the variant nucleotide sequences encoding variant proteins of YjjK proteins can be obtained by PCR (polymerase chain reaction; refer to White T. J. et al., The polymerase chain reaction, *Trends Genet.*, 1989, 5:185-189) utilizing primers prepared based on the nucleotide sequence of the yjjK gene; or the site-directed mutagenesis method by treating a DNA containing the wild-type or mutant yjjK gene in vitro, for example, with hydroxylamine, or a method for treating a microorganism, for example, a bacterium belonging to the family Enterobacteriaceae harboring the wild-type or mutant yjjK gene with ultraviolet (UV) irradiation or a mutating agent such as N-methyl-N'-nitro-N-nitrosoguanidine (NTG) and nitrous acid usually used for the such treatment; or chemically synthesized as full-length gene structure. Genes encoding the YjjK protein or its variant proteins of other microorganisms can be obtained in a similar manner.

The phrase "a wild-type protein" can mean a native protein naturally produced by a wild-type or parent bacterial strain of the family Enterobacteriaceae, for example, by the wild-type *E. coli* MG1655 strain. A wild-type protein can be encoded by the wild-type, or non-modified, gene naturally occurring in genome of a wild-type bacterium.

The phrase "operably linked to a gene" can mean that the regulatory region(s) is/are linked to the nucleotide sequence of the nucleic acid molecule or gene of interest in a manner which allows for expression (e.g., enhanced, increased, constitutive, basal, antiterminated, attenuated, deregulated, decreased or repressed expression) of the nucleotide sequence, preferably expression of a gene product encoded by the nucleotide sequence.

The bacterium as described herein can be obtained by attenuating expression of the yjjK gene in a bacterium inherently having an ability to produce an L-amino acid. Alternatively, the bacterium as described herein can be obtained by imparting the ability to produce an L-amino acid to a bacterium already having attenuated expression of the yjjK gene.

The bacterium can have, in addition to the properties already mentioned, other specific properties such as various nutrient requirements, drug resistance, drug sensitivity, and drug dependence, without departing from the scope of the present invention.

2. Method

A method of the present invention includes the method for producing an L-amino acid such as L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine, or a salt thereof, or a mixture thereof. The method for producing an L-amino acid can include the steps of cultivating the bacterium in a culture medium to allow the L-amino acid to be produced, excreted, or accumulated in the culture medium, and collecting the L-amino acid from the culture medium and/or the bacterial cells. Collected amino acid can be further purified. The L-amino acid can be produced in a salt form thereof. For example, sodium, potassium, ammonium, and the like salts of the L-amino acid can be produced by the method.

The cultivation of the bacterium, and collection and purification of L-amino acid or a salt thereof from the medium and the like may be performed in a manner similar to conventional fermentation methods wherein L-amino acid is produced using a microorganism. The culture medium for production of the L-amino acid can be either a synthetic or natural medium such as a typical medium that contains a carbon source, a nitrogen source, a sulphur source, inorganic ions, and other organic and inorganic components as required. As the carbon source, saccharides such as glucose, lactose, galactose, fructose, sucrose, arabinose, maltose, xylose, trehalose, ribose, and hydrolyzates of starches; alcohols such as glycerol, mannitol, and sorbitol; organic acids such as gluconic acid, fumaric acid, citric acid, malic acid, and succinic acid; and the like can be used. As the nitrogen source, inorganic ammonium salts such as ammonium sulfate, ammonium chloride, and ammonium phosphate; organic nitrogen such as of soy bean hydrolyzates; ammonia gas; aqueous ammonia; and the like can be used. The sulphur source can include ammonium sulphate, magnesium sulphate, ferrous sulphate, manganese sulphate, and the like. Vitamins such as vitamin B1, required substances, for example, organic nutrients such as nucleic acids such as adenine and RNA, or yeast extract, and the like may be present in appropriate, even if trace, amounts. Other than these, small amounts of calcium phosphate, iron ions, manganese ions, and the like may be added, if necessary.

Cultivation can be performed under aerobic conditions for 16 to 72 h, or for 16 to 65 h; the culture temperature during cultivation can be controlled within 30 to 45° C., or within 30 to 37° C.; and the pH can be adjusted between 5 and 8, or between 6 and 7.5. The pH can be adjusted by using an inorganic or organic acidic or alkaline substance, as well as ammonia gas.

After cultivation, solids such as cells and cell debris can be removed from the liquid medium by centrifugation or membrane filtration, and then the target L-amino acid or a salt thereof can be recovered from the fermentation liquor by any combination of conventional techniques such as concentration, ion-exchange chromatography, and crystallization.

The collected target L-amino acid may contain microbial cells, medium components, moisture, and by-product metabolites of the microorganism in addition to the target substance. Purity of the collected target substance is 50% or higher, 85% or higher, or 95% or higher (U.S. Pat. No. 5,431, 933, Japanese Patent No. 1214636, U.S. Pat. Nos. 4,956,471, 4,777,051, 4,946,654, 5,840,358, 6,238,714, U.S. Patent Published Application No. 2005/0025878).

EXAMPLES

The present invention will be more precisely explained below with reference to the following non-limiting Examples.

Example 1

Construction of the *E. coli* Strain in which the yjjK Gene is Inactivated

The yjjK gene was deleted using the method developed by Datsenko K. A. and Wanner B. L. (*Proc. Natl. Acad. Sci. USA,* 2000, 97(12), 6640-6645) called "λRed/ET-mediated integration". According to this method, the PCR primers P1 (SEQ ID NO: 3) and P2 (SEQ ID NO: 4), which are homologous to regions adjacent to the yjjK gene at either end, and the gene conferring kanamycin resistance ($Km^R$) in the template chromosome, were constructed. The chromosome of *E. coli* MG1655 ΔattBphi80 native IS5.11::LattBphi80-$Km^R$-Ratt-Bphi80 (Minaeva N. I. et al., Dual-In/Out strategy for genes integration into bacterial chromosome: a novel approach to step-by-step construction of plasmid-less marker-less recombinant *E. coli* strains with predesigned genome structure. *BMC Biotechnol.,* 2008, 8:63) was used as the template. Conditions for PCR were as follows: initial denaturation for 3 min at 95° C.; profile for two first cycles: 1 min at 95° C., 30 sec at 34° C., 40 sec at 72° C.; profile for the last 30 cycles: 30 sec at 95° C., 30 sec at 50° C., 40 sec at 72° C.; final step: 5 min at 72° C.

The obtained PCR product 1 (SEQ ID NO: 5) (1,922 bp) was purified by the agarose gel electrophoresis and used for electroporation of the strain *E. coli* MG1655 ΔattBphi80 native (Minaeva N. I. et al., *BMC Biotechnol.,* 2008, 8:63) containing the plasmid pKD46 with a temperature-sensitive replication origin. The plasmid pKD46 (Datsenko K. A. and Wanner B. L., *Proc. Natl. Acad. Sci. USA,* 2000, 97:12:6640-45) includes the 2,154 nucleotides (31088-33241) DNA-fragment of phage λ (GenBank accession No. J02459) and contains genes of the λRed/ET-mediated integration system (γ, β, exo genes) under the control of arabinose-inducible promoter $P_{araB}$. The plasmid pKD46 is necessary to integrate the PCR-product into the chromosome of strain *E. coli* MG1655ΔattBphi80 native.

Electrocompetent cells were prepared as follows: *E. coli* MG1655 ΔattBphi80 native was grown overnight at 30° C. in LB-medium containing ampicillin (100 mg/L), and the culture was diluted 100 times with 5 mL of SOB-medium (Sambrook J., Fritsch E. F. and Maniatis T., "Molecular Cloning: A Laboratory Manual", $2^{nd}$ ed., Cold Spring Harbor Laboratory Press (1989)) containing ampicillin and L-arabinose (1 mM). The obtained culture was grown with aeration at 30° C. to $OD_{600}$ of ~0.6 and then made electrocompetent by concentrating 100-fold and washing three times with ice-cold deionized $H_2O$. Electroporation was performed using 70 μL of cells and ~100 ng of the PCR product 1. Cells were incubated in 1 mL of SOC-medium (Sambrook J., Fritsch E. F. and Maniatis T., "Molecular Cloning: A Laboratory Manual", $2^{nd}$ ed., Cold Spring Harbor Laboratory Press (1989)) at 37° C. for 2.5 h, plated onto plates containing the lysogenic broth (Sambrook, J. and Russell, D. W. "Molecular Cloning: A Laboratory Manual", $3^{rd}$ ed., Cold Spring Harbor Laboratory Press (2001)), agar (1.5%) and kanamycin (50 mg/L), and grown at 37° C. to select $Km^R$ recombinants. Two passages on L-agar with kanamycin (50 mg/L) at 42° C. were performed to eliminate the pKD46 plasmid, and the colonies obtained were tested for sensitivity to ampicillin using standard procedure. Thus the *E. coli* MG1655 ΔattBphi80 native ΔyjjK::$Km^R$ strain was obtained.

Verification of the yjjK Gene Deletion by PCR

Mutants containing deletion of the yjjK gene and marked with kanamycin-resistance gene (kan) were verified by PCR. Locus-specific primers P3 (SEQ ID NO: 6) and P4 (SEQ ID NO: 7) were used for PCR. Conditions were as follows: initial denaturation for 3 min at 94° C.; profile for the 30 cycles: 30 sec at 94° C., 30 sec at 53° C., 2 min at 72° C.; final step: 6 min at 72° C. The PCR product 2 (SEQ ID NO: 8) (1,783 bp) was obtained, when the chromosomal DNA from parental yjjK strain *E. coli* MG1655 ΔattBphi80 native was used as the template. The PCR product 3 (SEQ ID NO: 9) (1,989 bp) was obtained, when the chromosomal DNA from mutant MG1655 ΔattBphi80 native ΔyjjK::$Km^R$ strain was used as the template.

Example 2

Construction of the *E. coli* L-valine-producing Strain in which the yjjK Gene is Inactivated The yjjK gene was deleted from the *E. coli* H-81 L-valine-producing strain using the P1-transduction (Miller J. H. "Experiments in molecular genetics", Cold Spring Harbor Laboratory, Cold Spring Harbor (1972)). The strain H-81 (EP1239041 A2) was deposited in the Russian National Collection of Industrial Microorganisms (VKPM) (Russian Federation, 117545 Moscow, $1^{st}$ Dorozhny proezd, 1) on Jan. 30, 2001 under the accession number VKPM B-8066, and it was then converted to an international deposit under the provisions of the Budapest Treaty on Feb. 1, 2002. The *E. coli* MG1655 ΔattBphi80 native ΔyjjK::$Km^R$ strain (Example 1) was used as the donor. The yjjK-deficient mutants of *E. coli* H-81 were selected on the plates containing the lysogenic broth (Sambrook, J. and Russell, D. W. "Molecular Cloning: A Laboratory Manual", $3^{rd}$ ed., Cold Spring Harbor Laboratory Press (2001)), agar (1.5%) and kanamycin (50 mg/L). Thus the *E. coli* H-81ΔyjjK::$Km^R$ strain was obtained. The ΔyjjK::$Km^R$ deletion was verified by PCR as described in Example 1.

Example 3

Production of L-valine by the *E. coli* H-81ΔyjjK::$Km^R$ Strain

The modified *E. coli* H-81ΔyjjK::$Km^R$ and the control *E. coli* H-81 strains were each cultivated at 32° C. for 18 hours in Luria-Bertani broth (also referred to as lysogenic broth as described in Sambrook, J. and Russell, D. W. "Molecular Cloning: A Laboratory Manual", 3rd ed., Cold Spring Harbor Laboratory Press (2001)). Then, 0.2 mL of the obtained culture was inoculated into 2 mL of a fermentation medium in 20×200-mm test tubes and cultivated at 30° C. for 48 hours on a rotary shaker at 250 rpm.

The composition of the fermentation medium (g/L) was as follows:

| | |
|---|---|
| Glucose | 60.0 |
| (NH$_4$)$_2$SO$_4$ | 15.0 |
| KH$_2$PO$_4$ | 1.5 |
| MgSO$_4$•7H$_2$O | 1.0 |
| Thiamine-HCl | 0.1 |
| CaCO$_3$ | 25.0 |
| LB medium | 10% (v/v) |

The fermentation medium was sterilized at 116° C. for 30 min, except that glucose and CaCO$_3$ were sterilized separately as follows: glucose at 110° C. for 30 min and CaCO$_3$ at 116° C. for 30 min. The pH was adjusted to 7.0 by KOH solution.

After cultivation, accumulated L-valine was measured using thin-layer chromatography (TLC). TLC plates (10×20 cm) were coated with 0.11-mm layers of Sorbfil silica gel containing non-fluorescent indicator (Sorbpolymer, Krasnodar, Russian Federation). Samples were applied to the plates with the Camag Linomat 5 sample applicator. The Sorbfil plates were developed with a mobile phase consisting of iso-propanol:ethylacetate:25% aqueous ammonia:water (16:16:5:10, v/v). A solution of ninhydrin (2%, w/v) in acetone was used as the visualizing reagent. After development, plates were dried and scanned with the Camag TLC Scanner 3 in absorbance mode with detection at 520 nm using winCATS software (version 1.4.2).

The results of 9 independent test-tube fermentations are shown in Table 1. As it can be seen from the Table 1, the modified E. coli H-81ΔyjjK::Km$^R$ strain was able to produce a higher amount of L-valine (Val) as compared with the parent E. coli H-81 strain.

TABLE 1

Production of L-valine.

| Strain | OD$_{550}$ | Val, g/L |
|---|---|---|
| E. coli H-81 (control) | 23 ± 1 | 8.7 ± 0.6 |
| E. coli H-81ΔyjjK::Km$^R$ | 24 ± 1 | 9.4 ± 0.1 |

Example 4

Construction of the E. coli L-histidine-producing Strain in which the yjjK Gene is Inactivated To test the effect of inactivation of the yjjK gene on L-histidine production, the DNA-fragments from the chromosome of the above-described E. coli MG1655 ΔattBphi80 native ΔyjjK::Km$^R$ strain (Example 1) were transferred to the L-histidine-producing strain E. coli MG1655+hisGr hisL'_Δ ΔpurR using the P1-transduction (Miller J. H. "Experiments in molecular genetics", Cold Spring Harbor Laboratory, Cold Spring Harbor (1972)) as described in Example 2. The ΔyjjK::Km$^R$ deletion was verified by PCR. Thus the E. coli MG1655+hisGr hisL'_Δ ΔpurR ΔyjjK::Km$^R$ strain was obtained.

The strain E. coli MG1655+hisGr hisL'_Δ ΔpurR has been described in RU2119536 C1; Doroshenko V. G. et al., The directed modification of Escherichia coli MG1655 to obtain histidine-producing mutants, *Prikl. Biochim. Mikrobiol. (Russian)*, 2013, 49(2):149-154.

Example 5

Production of L-histidine by the E. coli MG1655+hisGr hisL'_Δ ΔpurR Strain

The modified E. coli MG1655+hisGr hisL'_Δ ΔpurR ΔyjjK::Km$^R$ and the control E. coli MG1655+hisGr hisL'_Δ ΔpurR strains were each cultivated at 30° C. for 3 hours in 2 mL L-broth (Sambrook, J. and Russell, D. W. "Molecular Cloning: A Laboratory Manual", 3rd ed., Cold Spring Harbor Laboratory Press (2001)). Then, 0.1 mL of the obtained cultures were inoculated into 2 mL of fermentation medium in 20×200-mm test tubes and cultivated for 65 h at 30° C. on a rotary shaker (250 rpm).

The composition of the fermentation medium (g/L) was as follows:

| | |
|---|---|
| Glucose | 50.0 |
| Mameno* | 0.2 (as the amount of nitrogen) |
| L-aspartate | 1.0 |
| (NH$_4$)$_2$SO$_4$ | 18.0 |
| KCl | 1.0 |
| KH$_2$PO$_4$ | 0.5 |
| MgSO$_4$•7H$_2$O | 0.4 |
| FeSO$_4$•7H$_2$O | 0.02 |
| MnSO$_4$•5H$_2$O | 0.02 |
| ZnSO$_4$•7H$_2$O | 0.02 |
| Adenosine | 0.2 |
| Thiamine-HCl | 0.001 |
| Betaine | 2.0 |
| CaCO$_3$ | 60.0 |

*Mameno is the soybean meal hydrolysate (Ajinomoto Co, Inc.).
Glucose, magnesium sulphate, betaine, and CaCO$_3$ were sterilized separately. The pH was adjusted to 6.0 by 6M KOH solution before sterilization.

After cultivation, accumulated L-histidine was measured using thin-layer chromatography (TLC). TLC plates (10×20 cm) were coated with 0.11-mm layers of Sorbfil silica gel containing non-fluorescent indicator (Sorbpolymer, Krasnodar, Russian Federation). Samples were applied to the plates with the Camag Linomat 5 sample applicator. The Sorbfil plates were developed with a mobile phase consisting of iso-propanol:acetone:25% aqueous ammonia:water (6:6:1.5:1, v/v). A solution of ninhydrin (2%, w/v) in acetone was used as the visualizing reagent. After development, plates were dried and scanned with the Camag TLC Scanner 3 in absorbance mode with detection at 520 nm using winCATS software (version 1.4.2).

The results of 7 independent test-tube fermentations are shown in Table 2. As it can be seen from the Table 2, the modified E. coli MG1655+hisGr hisL'_Δ ΔpurR ΔyjjK::Km$^R$ strain was able to produce a higher amount of L-histidine (His) as compared with the parent E. coli MG1655+hisGr hisL'_Δ ΔpurR strain.

TABLE 2

Production of L-histidine.

| Strain | OD$_{550}$ | His, g/L |
|---|---|---|
| E. coli MG1655 + hisGr hisL'_Δ ΔpurR (control) | 18.3 ± 0.5 | 0.90 ± 0.05 |
| E. coli MG1655 + hisGr hisL'_Δ ΔpurR ΔyjjK::Km$^R$ | 19.1 ± 1.0 | 1.10 ± 0.10 |

Example 6

Production of L-arginine by *E. coli* 382ΔyjjK Strain

To test the effect of inactivation of the yjjK gene on L-arginine production, the DNA-fragments from the chromosome of the above-described *E. coli* MG1655 ΔattBphi80 native ΔyjjK::Km$^R$ are transferred to the arginine-producing *E. coli* strain 382 by P1-transduction (Miller, J. H. "Experiments in Molecular Genetics", Cold Spring Harbor Lab. Press, Plainview, N.Y. (1972)) to obtain the strain 382ΔyjjK. The strain 382 was deposited in the Russian National Collection of Industrial Microorganisms (VKPM) (Russian Federation, 117545 Moscow, 1$^{st}$ Dorozhny proezd, 1) on Apr. 10, 2000 under the accession number VKPM B-7926 and then converted to a deposit under the Budapest Treaty on May 18, 2001.

Both *E. coli* strains, 382 and 382ΔyjjK, are separately cultivated with shaking (220 rpm) at 37° C. for 18 h in 3 mL of nutrient broth, and 0.3 mL of the obtained cultures are inoculated into 2 mL of a fermentation medium in 20×200-mm test tubes and cultivated at 32° C. for 48 h on a rotary shaker (220 rpm).

After the cultivation, the amount of L-arginine which accumulates in the medium is determined by paper chromatography using a mobile phase consisting of n-butanol:acetic acid:water=4:1:1 (v/v). A solution of ninhydrin (2%) in acetone is used as a visualizing reagent. A spot containing L-arginine is cut out, L-arginine is eluted with 0.5% water solution of $CdCl_2$, and the amount of L-arginine is estimated spectrophotometrically at 540 nm.

The composition of the fermentation medium (g/L) is as follows:

| | |
|---|---|
| Glucose | 48.0 |
| $(NH_4)_2SO_4$ | 35.0 |
| $KH_2PO_4$ | 2.0 |
| $MgSO_4 \cdot 7H_2O$ | 1.0 |
| Thiamine-HCl | 0.0002 |
| Yeast extract | 1.0 |
| L-isoleucine | 0.1 |
| $CaCO_3$ | 5.0 |

Glucose and magnesium sulfate are sterilized separately. $CaCO_3$ is dry-heat sterilized at 180° C. for 2 h. The pH is adjusted to 7.0.

Example 7

Production of L-cysteine by *E. coli* JM15(ydeD)ΔyjjK

To test the effect of inactivation of the yjjK gene on L-cysteine production, the DNA fragments from the chromosome of the above-described *E. coli* MG1655 ΔattBphi80 native ΔyjjK::Km$^R$ are transferred to the *E. coli* L-cysteine-producing strain JM15(ydeD) by P1-transduction to obtain the strain JM15(ydeD)ΔyjjK.

*E. coli* JM15(ydeD) is a derivative of *E. coli* JM15 (U.S. Pat. No. 6,218,168), which is transformed with DNA having the ydeD gene encoding a membrane protein, and is not involved in a biosynthetic pathway of any L-amino acid (U.S. Pat. No. 5,972,663).

Fermentation conditions and procedure for evaluation of L-cysteine production were described in detail in Example 6 of U.S. Pat. No. 6,218,168.

Example 8

Production of L-glutamic Acid by *E. coli* VL334thrC$^+$ΔyjjK

To test the effect of inactivation of the yjjK gene on L-glutamic acid production, the DNA fragments from the chromosome of the above-described *E. coli* MG1655 ΔattBphi80 native ΔyjjK::Km$^R$ are transferred to the *E. coli* L-glutamate-producing strain VL334thrC$^+$ (EP1172433 A1) by P1-transduction to obtain the strain VL334thrC$^+$ΔyjjK. The strain VL334thrC$^+$ has been deposited in the Russian National Collection of Industrial Microorganisms (VKPM) (Russian Federation, 117545 Moscow, 1 Dorozhny proezd, 1) on Dec. 6, 2004 under the accession number B-8961 and then converted to a deposit under the Budapest Treaty on Dec. 8, 2004.

*E. coli* strains, VL334thrC$^+$ and VL334thrC$^+$ ΔyjjK, are separately cultivated for 18-24 h at 37° C. on L-agar plates. Then, one loop of the cells is transferred into test tubes containing 2 mL of fermentation medium.

The composition of the fermentation medium (g/L) is as follows:

| | |
|---|---|
| Glucose | 60.0 |
| $(NH_4)_2SO_4$ | 25.0 |
| $KH_2PO_4$ | 2.0 |
| $MgSO_4 \cdot 7H_2O$ | 1.0 |
| Thiamine-HCl | 0.1 |
| L-isoleucine | 0.07 |
| $CaCO_3$ | 25.0 |

Glucose and $CaCO_3$ are sterilized separately. The pH is adjusted to 7.2.

Cultivation is carried out at 30° C. for 3 days with shaking. After the cultivation, the amount of L-glutamic acid, which is produced, is determined by paper chromatography using a mobile phase consisting of n-butanol:acetic acid:water=4:1:1 with subsequent staining by ninhydrin (1% solution in acetone), elution of the compounds in 50% ethanol with 0.5% $CdCl_2$ and further estimation of L-glutamic acid at 540 nm.

Example 9

Production of L-leucine by *E. coli* 57ΔyjjK

To test the effect of inactivation of the yjjK gene on L-leucine production, the DNA fragments from the chromosome of the above-described *E. coli* MG1655 ΔattBphi80 native ΔyjjK::Km$^R$ are transferred to the *E. coli* L-leucine-producing strain 57 (VKPM B-7386, U.S. Pat. No. 6,124,121) by P1-transduction to obtain the strain 57ΔyjjK. The strain 57 has been deposited in the Russian National Collection of Industrial Microorganisms (VKPM) (Russian Federation, 117545 Moscow, 1$^{st}$ Dorozhny proezd, 1) on May 19, 1997 under the accession number B-7386.

*E. coli* strains, 57 and 57ΔyjjK, are separately cultivated for 18-24 h at 37° C. on L-agar plates. To obtain a seed culture, the strains are grown on a rotary shaker (250 rpm) at 32° C. for 18 h in 20×200-mm test tubes containing 2 mL of L-broth (Sambrook, J. and Russell, D. W. (2001) "Molecular Cloning: A Laboratory Manual", 3$^{rd}$ ed., Cold Spring Harbor Laboratory Press) supplemented with sucrose (4%). Then, the fermentation medium is inoculated with 0.2 mL of seed material (10%). The fermentation is performed in 2 mL of a minimal fermentation medium in 20×200-mm test tubes. Cells are grown for 48-72 h at 32° C. with shaking at 250 rpm. The amount of L-leucine which accumulates in the medium is measured by paper chromatography using a mobile phase consisting of n-butanol:acetic acid:water=4:1:1.

The composition of the fermentation medium (g/L) is as follows:

| | |
|---|---|
| Glucose | 60.0 |
| $(NH_4)_2SO_4$ | 25.0 |
| $K_2HPO_4$ | 2.0 |
| $MgSO_4 \cdot 7H_2O$ | 1.0 |
| Thiamine-HCl | 0.01 |
| $CaCO_3$ | 25.0 |

Glucose is sterilized separately. $CaCO_3$ is dry-heat sterilized at 180° C. for 2 h. The pH is adjusted to 7.2.

Example 10

Production of L-lysine by *E. coli* AJ11442ΔyjjK

To test the effect of inactivation of the yjjK gene on L-lysine production, the DNA fragments from the chromosome of the above-described *E. coli* MG1655 ΔattBphi80 native ΔyjjK::$Km^R$ are transferred to the L-lysine-producing *E. coli* strain AJ11442 by P1-transduction to obtain the AJ11442ΔyjjK strain. The strain AJ11442 was deposited in Fermentation Research Institute, Agency of Industrial Science and Technology (currently, Incorporated Administrative Agency, National Institute of Technology and Evaluation, International Patent Organism (NITE IPOD), Kazusakamatari, Kisarazu-shi, Chiba-ken 292-0818, JAPAN) on May 5, 1981 under a deposition number of FERM P-5084, and transferred from the original deposition to international deposition based on Budapest Treaty on Oct. 29, 1987, and has been deposited as deposition number of FERM BP-1543. The pCABD2 plasmid includes the dapA gene encoding dihydrodipicolinate synthase having a mutation which desensitizes feedback inhibition by L-lysine, the lysC gene encoding aspartokinase III having a mutation which desensitizes feedback inhibition by L-lysine, the dapB gene encoding dihydrodipicolinate reductase, and the ddh gene encoding diaminopimelate dehydrogenase (U.S. Pat. No. 6,040,160).

*E. coli* strains, AJ11442 and AJ11442ΔyjjK, are separately cultivated in L-medium containing streptomycin (20 mg/L) at 37° C., and 0.3 mL of the obtained culture is inoculated into 20 mL of the fermentation medium containing the required drugs in a 500-mL flask. The cultivation is carried out at 37° C. for 16 h by using a reciprocal shaker at the agitation speed of 115 rpm. After the cultivation, the amounts of L-lysine and residual glucose in the medium are measured by a known method (Biotech-analyzer AS210, Sakura Seiki Co.). Then, the yield of L-lysine is calculated relative to consumed glucose for each of the strains.

The composition of the fermentation medium (g/L) is as follows:

| | |
|---|---|
| Glucose | 40.0 |
| $(NH_4)_2SO_4$ | 24.0 |
| $K_2HPO_4$ | 1.0 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Yeast extract | 2.0 |

The pH is adjusted to 7.0 by KOH and the medium is autoclaved at 115° C. for 10 min. Glucose and magnesium sulfate are sterilized separately. $CaCO_3$ is dry-heat sterilized at 180° C. for 2 h and added to the medium for a final concentration of 30 g/L.

Example 11

Production of L-phenylalanine by *E. coli* AJ12739ΔyjjK

To test the effect of inactivation of the yjjK gene on L-phenylalanine production, the DNA fragments from the chromosome of the above-described *E. coli* MG1655 ΔattBphi80 native ΔyjjK::$Km^R$ are transferred to the phenylalanine-producing *E. coli* strain AJ12739 by P1-transduction to obtain strain AJ12739ΔyjjK. The strain AJ12739 has been deposited in the Russian National Collection of Industrial Microorganisms (VKPM) (Russian Federation, 117545 Moscow, $1^{st}$ Dorozhny proezd, 1) on Nov. 6, 2001 under the accession number VKPM B-8197 and then converted to a deposit under the Budapest Treaty on Aug. 23, 2002.

*E. coli* strains, AJ12739 and AJ12739ΔyjjK, are separately cultivated at 37° C. for 18 h in a nutrient broth, and 0.3 mL of the obtained culture is each inoculated into 3 mL of a fermentation medium in 20×200-mm test tubes and cultivated at 37° C. for 48 h with shaking on a rotary shaker. After cultivation, the amount of L-phenylalanine which accumulates in the medium is determined by thin layer chromatography (TLC). The 10×15-cm TLC plates coated with 0.11-mm layers of Sorbfil silica gel containing non-fluorescent indicator (Stock Company Sorbpolymer, Krasnodar, Russian Federation) are used. The Sorbfil plates are developed with a mobile phase consisting of propan-2-ol:ethylacetate:25% aqueous ammonia:water=40:40:7:16 (v/v). A solution of ninhydrin (2%) in acetone is used as a visualizing reagent.

The composition of the fermentation medium (g/L) is as follows:

| | |
|---|---|
| Glucose | 40.0 |
| $(NH_4)_2SO_4$ | 16.0 |
| $K_2HPO_4$ | 0.1 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Thiamine-HCl | 0.0002 |
| Yeast extract | 2.0 |
| Tyrosine | 0.125 |
| $CaCO_3$ | 20.0 |

Glucose and magnesium sulfate are sterilized separately. $CaCO_3$ is dry-heat sterilized at 180° C. for 2 h. The pH is adjusted to 7.0.

Example 12

Production of L-proline by *E. coli* 702ilvAΔyjjK

To test the effect of inactivation of the yjjK gene on L-proline production, the DNA fragments from the chromosome of the above-described *E. coli* MG1655 ΔattBphi80 native ΔyjjK::$Km^R$ are transferred to the proline-producing *E. coli* strain 702ilvA by P1-transduction to obtain the strain 702ilvAΔyjjK. The strain 702ilvA was deposited in the Russian National Collection of Industrial Microorganisms (VKPM) (Russian Federation, 117545 Moscow, $1^{st}$ Dorozhny proezd, 1) on Jul. 18, 2000 under the accession number VKPM B-8012 and was then converted to a deposit under the Budapest Treaty on May 18, 2001.

*E. coli* strains, 702ilvA and 702ilvAΔyjjK, are separately cultivated for 18-24 h at 37° C. on L-agar plates. Then, these strains are cultivated under the same conditions as in Example 8 (Production of L-glutamic acid).

Example 13

Production of L-threonine by *E. coli* B-3996ΔyjjK

To test the effect of inactivation of the yjjK gene on L-threonine production, the DNA fragments from the chromosome of the above-described *E. coli* MG1655 ΔattBphi80 native ΔyjjK::Km$^R$ are transferred to the L-threonine-producing *E. coli* strain VKPM B-3996 by P1-transduction to obtain the strain B-3996ΔyjjK. The strain B-3996 was deposited on Nov. 19, 1987 in the All-Union Scientific Center of Antibiotics (Russian Federation, 117105 Moscow, Nagatinskaya Street, 3-A) under the accession number RIA 1867. The strain was also deposited in the Russian National Collection of Industrial Microorganisms (VKPM) (Russian Federation, 117545 Moscow, 1$^{st}$ Dorozhny proezd, 1) under the accession number B-3996.

Both *E. coli* strains, B-3996 and B-3996ΔyjjK, are separately cultivated for 18-24 h at 37° C. on L-agar plates. To obtain a seed culture, the strains are grown on a rotary shaker (250 rpm) at 32° C. for 18 h in 20×200-mm test tubes containing 2 mL of L-broth (Sambrook, J. and Russell, D. W. (2001) "Molecular Cloning: A Laboratory Manual", 3$^{rd}$ ed., Cold Spring Harbor Laboratory Press) supplemented with glucose (4%). Then, the fermentation medium is inoculated with 0.2 mL (10%) of seed material. The fermentation is performed in 2 mL of minimal medium in 20×200-mm test tubes. Cells are grown for 65 h at 32° C. with shaking at 250 rpm.

After cultivation, the amount of L-threonine which accumulates in the medium is determined by paper chromatography using a mobile phase consisting of n-butanol:acetic acid:water=4:1:1 (v/v). A solution of ninhydrin (2%) in acetone is used as a visualizing reagent. A spot containing L-threonine is cut out, L-threonine is eluted with 0.5% water solution of CdCl$_2$, and the amount of L-threonine is estimated spectrophotometrically at 540 nm.

The composition of the fermentation medium (g/L) is as follows:

| | |
|---|---|
| Glucose | 80.0 |
| (NH$_4$)$_2$SO$_4$ | 22.0 |
| NaCl | 0.8 |
| KH$_2$PO$_4$ | 2.0 |
| MgSO$_4$•7H$_2$O | 0.8 |
| FeSO$_4$•7H$_2$O | 0.02 |
| MnSO$_4$•5H$_2$O | 0.02 |
| Thiamine-HCl | 0.0002 |
| Yeast extract | 1.0 |
| CaCO$_3$ | 30.0 |

Glucose and magnesium sulfate are sterilized separately. CaCO$_3$ is sterilized by dry-heat at 180° C. for 2 h. The pH is adjusted to 7.0. The antibiotic is introduced into the medium after sterilization.

Example 14

Production of L-tryptophan by *E. coli* SV164(pGH5)ΔyjjK

To test the effect of inactivation of the yjjK gene on L-tryptophan production, the DNA fragments from the chromosome of the above-described *E. coli* MG1655 ΔattBphi80 native ΔyjjK::Km$^R$ are transferred to the L-tryptophan-producing *E. coli* strain SV164(pGH5) by P1-transduction to obtain the strain SV164(pGH5)ΔyjjK. The strain SV164 has the trpE allele encoding anthranilate synthase free from feedback inhibition by tryptophan. The plasmid pGH5 harbors a mutant serA gene encoding phosphoglycerate dehydrogenase free from feedback inhibition by serine. The strain SV164(pGH5) was described in detail in U.S. Pat. No. 6,180,373 or EP0662143 B1.

*E. coli* strains, SV164(pGH5) and SV164(pGH5)ΔyjjK, are separately cultivated with shaking at 37° C. for 18 h in 3 mL of nutrient broth supplemented with tetracycline (20 mg/L, marker of pGH5 plasmid). The obtained cultures (0.3 mL each) are inoculated into 3 mL of a fermentation medium containing tetracycline (20 mg/L) in 20×200-mm test tubes, and cultivated at 37° C. for 48 h with a rotary shaker at 250 rpm. After cultivation, the amount of L-tryptophan which accumulates in the medium is determined by TLC as described in Example 11 (Production of L-phenylalanine). The fermentation medium components are listed in Table 3, but should be sterilized in separate groups (A, B, C, D, E, F, and H), as shown, to avoid adverse interactions during sterilization.

TABLE 3

| Solutions | Component | Final concentration, g/L |
|---|---|---|
| A | KH$_2$PO$_4$ | 1.5 |
| | NaCl | 0.5 |
| | (NH$_4$)$_2$SO$_4$ | 1.5 |
| | L-Methionine | 0.05 |
| | L-Phenylalanine | 0.1 |
| | L-Tyrosine | 0.1 |
| | Mameno* (as the amount of nitrogen) | 0.07 |
| B | Glucose | 40.0 |
| | MgSO$_4$•7H$_2$O | 0.3 |
| C | CaCl$_2$ | 0.011 |
| D | FeSO$_4$•7H$_2$O | 0.075 |
| | Sodium citrate | 1.0 |
| E | Na$_2$MoO$_4$•2H$_2$O | 0.00015 |
| | H$_3$BO$_3$ | 0.0025 |
| | CoCl$_2$•6H$_2$O | 0.00007 |
| | CuSO$_4$•5H$_2$O | 0.00025 |
| | MnCl$_2$•4H$_2$O | 0.0016 |
| | ZnSO$_4$•7H$_2$O | 0.0003 |
| F | Thiamine-HCl | 0.005 |
| G | CaCO$_3$ | 30.0 |
| H | Pyridoxine | 0.03 |

The pH of solution A is adjusted to 7.1 with NH$_4$OH.
*Mameno is the soybean meal hydrolysate (Ajinomoto Co, Inc.).

Example 15

Production of L-citrulline by *E. coli* 382ΔargGΔyjjK

To test the effect of inactivation of the yjjK gene on L-citrulline production, the DNA fragments from the chromosome of the above-described *E. coli* MG1655 ΔattBphi80 native ΔyjjK::Km$^R$ are transferred to the L-citrulline producing *E. coli* strain 382ΔargG by P1-transduction to obtain the strain 382ΔargGΔyjjK. The strain 382ΔargG is obtained by deletion of argG gene on the chromosome of 382 strain (VKPM B-7926) by the method initially developed by Datsenko K. A. and Wanner B. L. called "λRed/ET-mediated integration" (Datsenko K. A. and Wanner B. L., *Proc. Natl. Acad. Sci. USA*, 2000, 97(12):6640-6645). According to this procedure, the PCR primers homologous to both the region adjacent to the argG gene and the gene which confers antibiotic resistance in the template plasmid are constructed. The plasmid pMW118-λattL-cat-λattR (WO 05/010175) is used as the template in the PCR reaction.

Both *E. coli* strains, 382ΔargG and 382ΔargGΔyjjK, are separately cultivated with shaking at 37° C. for 18 h in 3 mL of nutrient broth, and 0.3 mL of the obtained cultures are inoculated into 2 mL of a fermentation medium in 20×200-mm test tubes and cultivated at 32° C. for 48 h on a rotary shaker.

After the cultivation, the amount of L-citrulline which accumulates in the medium is determined by paper chromatography using a mobile phase consisting of n-butanol:acetic acid:water=4:1:1 (v/v). A solution of ninhydrin (2%) in acetone is used as a visualizing reagent. A spot containing citrulline is cut out, L-citrulline is eluted with 0.5% water solution of $CdCl_2$, and the amount of L-citrulline is estimated spectrophotometrically at 540 nm.

The composition of the fermentation medium (g/L) is as follows:

| | |
|---|---|
| Glucose | 48.0 |
| $(NH_4)_2SO_4$ | 35.0 |
| $KH_2PO_4$ | 2.0 |
| $MgSO_4 \cdot 7H_2O$ | 1.0 |
| Thiamine-HCl | 0.0002 |
| Yeast extract | 1.0 |
| L-isoleucine | 0.1 |
| L-arginine | 0.1 |
| $CaCO_3$ | 5.0 |

Glucose and magnesium sulfate are sterilized separately. $CaCO_3$ is dry-heat sterilized at 180° C. for 2 h. The pH is adjusted to 7.0.

Example 16

Production of L-ornithine by E. coli 382ΔargFΔargIΔyjjK

To test the effect of inactivation of the yjjK gene on L-ornithine production, the DNA fragments from the chromosome of the above-described E. coli MG1655 ΔattBphi80 native ΔyjjK::$Km^R$ are transferred to the L-ornithine producing E. coli strain 382ΔargFΔargI by P1-transduction to obtain the strain 382ΔargFΔargIΔyjjK. The strain 382ΔargFΔargI is obtained by consecutive deletion of argF and argI genes on the chromosome of 382 strain (VKPM B-7926) by the method initially developed by Datsenko K. A. and Wanner B. L. called "λRed/ET-mediated integration" (Datsenko K. A. and Wanner B. L., *Proc. Natl. Acad. Sci. USA*, 2000, 97(12): 6640-6645). According to this procedure, two pairs of PCR primers homologous to both the region adjacent to the argF or argI gene and the gene which confers antibiotic resistance in the template plasmid are constructed. The plasmid pMW118-λattL-cat-λattR (WO 05/010175) is used as the template in the PCR reaction.

Both E. coli strains, 382ΔargFΔargI and 382ΔargFΔargIΔyjjK, are separately cultivated with shaking at 37° C. for 18 h in 3 mL of nutrient broth, and 0.3 mL of the obtained cultures are inoculated into 2 mL of a fermentation medium in 20×200-mm test tubes and cultivated at 32° C. for 48 h on a rotary shaker.

After the cultivation, the amount of ornithine which accumulates in the medium is determined by paper chromatography using a mobile phase consisting of n-butanol:acetic acid:water=4:1:1 (v/v). A solution of ninhydrin (2%) in acetone is used as a visualizing reagent. A spot containing ornithine is cut out, ornithine is eluted with 0.5% water solution of $CdCl_2$, and the amount of ornithine is estimated spectrophotometrically at 540 nm.

The composition of the fermentation medium (g/L) is as follows:

| | |
|---|---|
| Glucose | 48.0 |
| $(NH_4)_2SO_4$ | 35.0 |
| $KH_2PO_4$ | 2.0 |
| $MgSO_4 \cdot 7H_2O$ | 1.0 |
| Thiamine-HCl | 0.0002 |
| Yeast extract | 1.0 |
| L-isoleucine | 0.1 |
| L-arginine | 0.1 |
| $CaCO_3$ | 5.0 |

Glucose and magnesium sulfate are sterilized separately. $CaCO_3$ is dry-heat sterilized at 180° C. for 2 h. The pH is adjusted to 7.0.

While the invention has been described in detail with reference to preferred embodiments thereof, it will be apparent to one skilled in the art that various changes can be made, and equivalents employed, without departing from the scope of the invention. All the cited references herein are incorporated by reference as a part of this application.

What is claimed is:

1. A method for producing an L-amino acid comprising:
  (i) cultivating a bacterium belonging to the genus *Escherichia* in a culture medium to produce said L-amino acid in the culture medium, and
  (ii) collecting said L-amino acid from the culture medium, wherein said *Escherichia* bacterium has been modified to attenuate expression of a yjjK gene as compared with a corresponding non-modified *Escherichia* bacterium, wherein said modification to attenuate expression of said yjjK gene is by a method selected from the group consisting of inactivation of said yjjK gene on the chromosome of said *Escherichia* bacterium, modification of a region controlling expression of said yjjK gene on the chromosome of said *Escherichia* bacterium, and combinations thereof,
  wherein said yjjK gene comprises the nucleotide sequence of SEQ ID NO: 1 or a variant nucleotide sequence of SEQ ID NO: 1, wherein the variant nucleotide sequence is not less than 95% homologous to the nucleotide sequence of SEQ ID NO: 1.

2. The method according to claim 1, wherein said bacterium belongs to the species *Escherichia coli*.

3. The method according to claim 1, wherein said yjjK gene is deleted.

4. method according to claim 1, wherein said L-amino acid is selected from the group consisting of an aromatic L-amino acid and a non-aromatic L-amino acid.

5. method according to claim 4, wherein said aromatic L-amino acid is selected from the group consisting of L-phenylalanine, L-tryptophan, and L-tyrosine.

6. method according to claim 4, wherein said non-aromatic L-amino acid is selected from the group consisting of L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-proline, L-serine, L-threonine, and L-valine.

* * * * *